(12) United States Patent
Park et al.

(10) Patent No.: US 8,889,271 B2
(45) Date of Patent: Nov. 18, 2014

(54) COMPOUND CONTAINING A 5-MEMBERED HETEROCYCLE AND ORGANIC LIGHT-EMITTING DIODE USING SAME, AND TERMINAL FOR SAME

(75) Inventors: Junghwan Park, Seoul (KR); Daesung Kim, Yongin-si (KR); Jungcheol Park, Jinhae-si (KR); Kiwon Kim, Incheon (KR); Jinuk Ju, Uiryeong-gun (KR); Jangyeol Baek, Sacheon-si (KR); Soungyun Mun, Yongin-si (KR); Yongwook Park, Anyang-si (KR); Hwasoon Jung, Chuncheon-si (KR); Wonsam Kim, Seongnam-si (KR); Jihun Byun, Yongin-si (KR); Sungjin Park, Seongnam-si (KR); Eunkyung Kim, Jinju-si (KR); Daehyuk Choi, Suwon-si (KR); Dongha Kim, Seongnam-si (KR); Hansung Yu, Anyang-si (KR); Kwanhee Lee, Suwon-si (KR); Taeshick Kim, Yongin-si (KR); Daeyup Shin, Suwon-si (KR); Mikyung Kim, Yongin-si (KR); Dongheon Kim, Suwon-si (KR)

(73) Assignees: Duksan High Metal Co., Ltd., Ulsan (KR); Samsung Mobile Display Co., Ltd., Gyeonggi-do (KR)

( * ) Notice: Subject to any disclaimer, the term of this patent is extended or adjusted under 35 U.S.C. 154(b) by 238 days.

(21) Appl. No.: 13/320,189

(22) PCT Filed: Apr. 30, 2010

(86) PCT No.: PCT/KR2010/002735
§ 371 (c)(1),
(2), (4) Date: Dec. 15, 2011

(87) PCT Pub. No.: WO2010/131855
PCT Pub. Date: Nov. 18, 2010

(65) Prior Publication Data
US 2012/0080670 A1    Apr. 5, 2012

(30) Foreign Application Priority Data

| Nov. 26, 2006 | (KR) | 10-2009-0114964 |
| May 13, 2009 | (KR) | 10-2009-0041877 |
| May 20, 2009 | (KR) | 10-2009-0043994 |
| May 22, 2009 | (KR) | 10-2009-0044895 |
| May 22, 2009 | (KR) | 10-2009-0044896 |
| Nov. 26, 2009 | (KR) | 10-2009-0114960 |
| Nov. 26, 2009 | (KR) | 10-2009-0114963 |
| Nov. 26, 2009 | (KR) | 10-2009-0114965 |
| Nov. 26, 2009 | (KR) | 10-2009-0114966 |

(51) Int. Cl.
| H01L 51/54 | (2006.01) |
| H01L 51/00 | (2006.01) |
| C07D 209/82 | (2006.01) |
| C09K 11/06 | (2006.01) |
| H05B 33/14 | (2006.01) |
| H05B 33/10 | (2006.01) |
| C07D 495/04 | (2006.01) |
| H01L 51/50 | (2006.01) |

(52) U.S. Cl.
CPC ...... *C07D 495/04* (2013.01); *C09K 2211/1059* (2013.01); *H01L 51/0056* (2013.01); *H01L 51/0071* (2013.01); *C09K 2211/1044* (2013.01); *C07D 209/82* (2013.01); *C09K 11/06* (2013.01); *C09K 2211/1011* (2013.01); *C09K 2211/1092* (2013.01); *H05B 33/14* (2013.01); *Y02E 10/549* (2013.01); *C09K 2211/1007* (2013.01); *H05B 33/10* (2013.01); *C09K 2211/1029* (2013.01); *H01L 51/5012* (2013.01); *Y10S 428/917* (2013.01)
USPC ........... 428/690; 428/917; 313/504; 313/505; 313/506; 257/40; 257/E51.05; 257/E51.026; 257/E51.032; 548/304.1; 548/418; 548/440; 546/18; 546/79; 546/81; 546/101

(58) Field of Classification Search
USPC .................. 428/690, 917; 313/504, 505, 506; 257/40, E51.05, E51.026, E51.032; 548/304.1, 418, 440; 546/18, 79, 81, 546/101
See application file for complete search history.

(56) References Cited

U.S. PATENT DOCUMENTS

| 5,942,340 A | 8/1999 | Hu et al. |
| 7,592,622 B2 | 9/2009 | McKiernan et al. |
| 2004/0228964 A1* | 11/2004 | Ito et al. ......................... 427/64 |
| 2007/0252139 A1 | 11/2007 | Mckiernan et al. |

(Continued)

FOREIGN PATENT DOCUMENTS

| EP | 0906947 A1 | 4/1999 |
| KR | 10-2007-0051265 A | 5/2007 |

(Continued)

OTHER PUBLICATIONS

Yousuke Ooyama et al., "Synthesis and Solid-State Flurescence Properties of Structural Isomers of Novel Benzofuro [2,3-c] Oxazolocarbazole-Type Fluorescent Dyes", Department of Applied Checmistry, Graduate School of Engineering, Hiroshima University, 2007, pp. 3613-3621.
Teruhisa Tsuchimoto et al., "Indium-Catalyzed Annulation of 2-Aryl- and 2- Heteroarylindoles with Propargyl Ethers: Concise Synthesis and Photophysical Properties of Divorse Aryl- and Heteroaryl-Annulated[a] Carbazoles", Department of Applied Chemistry, School of Science and Technology, Meiji University, May 27, 2008, pp. 15823-15835.
Korean Office Action for Application No. 10-2009-0041877 mailed Mar. 22, 2011 (7 pages).

(Continued)

*Primary Examiner* — Gregory Clark
(74) *Attorney, Agent, or Firm* — The PL Law Group, PLLC

(57) ABSTRACT

Disclosed are a novel-structural compound including a 5-membered heterocycle, an organic electronic device using the same, and a terminal thereof.

10 Claims, 6 Drawing Sheets

(56) References Cited

U.S. PATENT DOCUMENTS

| 2008/0145708 | A1 | 6/2008 | Heil et al. | |
|---|---|---|---|---|
| 2008/0220285 | A1* | 9/2008 | Vestweber et al. | 428/690 |
| 2009/0096356 | A1 | 4/2009 | Murase et al. | |
| 2009/0253883 | A1 | 10/2009 | McKiernan et al. | |

FOREIGN PATENT DOCUMENTS

| KR | 10-2008-0003413 A | 1/2008 | | |
|---|---|---|---|---|
| KR | 10-2008-0015865 | 2/2008 | | |
| KR | 10-2008-0015865 A | 2/2008 | | |
| KR | 1020080015865 | * | 2/2008 | C09K 11/06 |
| KR | 10-2008-0055891 | 6/2008 | | |
| KR | 10-2008-0055891 A | 6/2008 | | |
| KR | 10-2010-0105099 | 9/2010 | | |
| KR | 10-2010-0118700 A | 11/2010 | | |
| KR | 10-2010-0018340 A | 2/2011 | | |
| WO | 01-14380 | 3/2001 | | |
| WO | 2006-122630 | 11/2006 | | |

OTHER PUBLICATIONS

Korean Office Action for Application No. 10-2009-0043994 mailed Apr. 12, 2011 (6 pages).
Korean Office Action for Application No. 10-2009-0044895 mailed Apr. 12, 2011 (7 pages).
Korean Office Action for Application No. 10-2009-0044896 mailed Apr. 12, 2011 (7 pages).
Korean Office Action for Application No. 10-2009-0114960 mailed Aug. 29, 2011 (7 pages).
Korean Office Action for Application No. 10-2009-0114963 mailed Aug. 29, 2011 (6 pages.).
Korean Office Action for Application No. 10-2009-0114964 mailed Aug. 29, 2011 (6 pages).
Korean Office Action for Application No. 10-2009-0114965 mailed Aug. 29, 2011 (6 pages).
Korean Office Action for Application No. 10-2009-0114966 mailed Aug. 29, 2011 (6 pages).
Keiko Kawaguchi et al., "Synthesis, Structures, and Properties of Unsymmetrical Heteroacenes Containing Both Pyrrole and Furan Rings", Department of Chemistry and Biotechnology, Graduate School of Engineering, The University of Tokyo, Jan. 11, 2008, pp. 1199-1202.
Herve Royer et al., "Synthesis of Pentacyclic Heteroaromatic Systems Related to Indolocarbazoles Alkaloids", Group de Synthese Organique et Heterocyclique, University de Metz, 1998, pp. 1239-1251.
Arasambattu K. Mohanakrishnan et al., "A One Pot Synthesis of Annulated Cargbazole Analogs", Tetrahendron Letters, Department of Organic Checmistry, Unversity of Madras, Jul. 2008, pp. 5850-5854.
International Search Report (in English) and Written Opinion of the International Searching Authority (in Korean) for PCT/KR2010/002735, mailed Jan. 18, 2011; ISA/KR.
Office action mailed Aug. 13, 2014 from Korean Intellectual Property Office in a counterpart Korean patent application No. 10-2011-0147131.

* cited by examiner

COMPOUND CONTAINING A 5-MEMBERED HETEROCYCLE AND ORGANIC LIGHT-EMITTING DIODE USING SAME, AND TERMINAL FOR SAME

BACKGROUND OF THE INVENTION

1. Field of the Invention

The present invention relates to a compound containing a 5-membered heterocycle, an organic electronic device using the same, and a terminal thereof.

2. Description of the Prior Art

In general, an organic light emitting phenomenon indicates conversion of electric energy into light energy by means of an organic material. An organic electronic device using the organic light emitting phenomenon generally has a structure including an anode, a cathode, and an organic material layer interposed therebetween. Herein, in many cases, the organic material layer may have a multi-layered structure having respective different materials in order to improve efficiency and stability of an organic electronic device. For example, it may include a hole injection layer, a hole transport layer, a light emitting layer, an electron transport layer, an electron injection layer, and the like.

Materials used as an organic material layer in an organic electronic device may be classified into a light emitting material and a charge transport material, for example, a hole injection material, a hole transport material, an electron transport material, an electron injection material, etc. according to their functions. Then, the light emitting material may be divided into a high molecular weight type and a low molecular weight type according to their molecular weight, and may be divided into a fluorescent material from electronic singlet excited states and a phosphorescent material from electronic triplet excited states according to their light emitting mechanism. Further, the light emitting material can be classified into a blue, green or red light emitting material and a yellow or orange light emitting material required for giving a more natural color, according to a light emitting color.

Meanwhile, when only one material is used as a light emitting material, an efficiency of a device is lowered owing to a maximum luminescence wavelength being moved to a longer wavelength due to the interaction between the molecules, the deterioration of color purity and the reduction in light emitting efficiency. Therefore, a host/dopant system can be used as the light emitting material for the purpose of enhancing the color purity and the light emitting efficiency through energy transfer. It is based on the principle that if a small amount of a dopant having a smaller energy band gap than a host forming a light emitting layer is mixed with the light emitting layer, excitons which are generated in the light emitting layer are transported to the dopant, thus emitting a light having a high efficiency. Here, since the wavelength of the host is moved according to the wavelength of the dopant, a light having a desired wavelength can be obtained according the kind of the dopant.

In order to allow the organic electronic device to fully exhibit the above-mentioned excellent characteristics, a material constituting the organic material layer in the device, for example, a hole injection material, a hole transport material, a light emitting material, an electron transport material and an electron injection material should be essentially composed of a stable and efficient material. However, the development of a stable and efficient organic material layer material for the organic electronic device has not yet been fully realized. Accordingly, the development of new materials is continuously desired.

SUMMARY OF THE INVENTION

An object of the present invention is to provide a novel-structural compound including a 5-membered heterocycle, an organic electronic device using the same, and a terminal thereof, in which high efficiency, color purity improvement, and long lifetime of the light emitting device can be achieved due to the characteristics of the compound.

In accordance with an aspect of the present invention, there is provided a compound represented by Formula below.

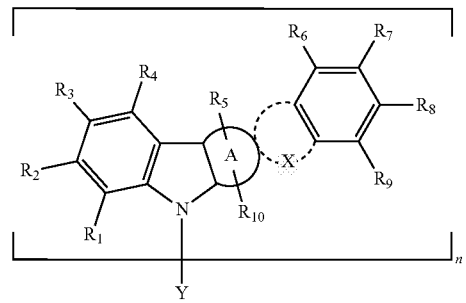

The inventive novel-structural compound including a 5-membered heterocycle may be used as a hole injection material, a hole transport material, a light emission material, and an electron transport material appropriate for a fluorescent or phosphorescent device of all colors (such as red, green, blue, white, etc.) according to synthesized compounds in an organic electronic device, and is useful as a host material for various colors of a phosphorescent dopant.

Accordingly, the present invention provides a novel-structural compound including a 5-membered heterocycle, an organic electronic device using the same, and a terminal thereof.

According to the present invention, the organic light emitting diode using the compound including a 5-membered heterocycle may be used as a hole injection material, a hole transport material, a light emission material, and an electron transport material appropriate for a fluorescent or phosphorescent device of all colors, and is useful as a host material for various colors of a phosphorescent dopant. Also, the compound may be used as a fluorescent or phosphorescent host material of a light emitting device, thereby significantly improving luminous efficiency, color purity, and lifetime.

BRIEF DESCRIPTION OF THE DRAWINGS

The above and other objects, features and advantages of the present invention will be more apparent from the following detailed description taken in conjunction with the accompanying drawings, in which.

DETAILED DESCRIPTION OF THE PREFERRED EMBODIMENTS

Figure 1:
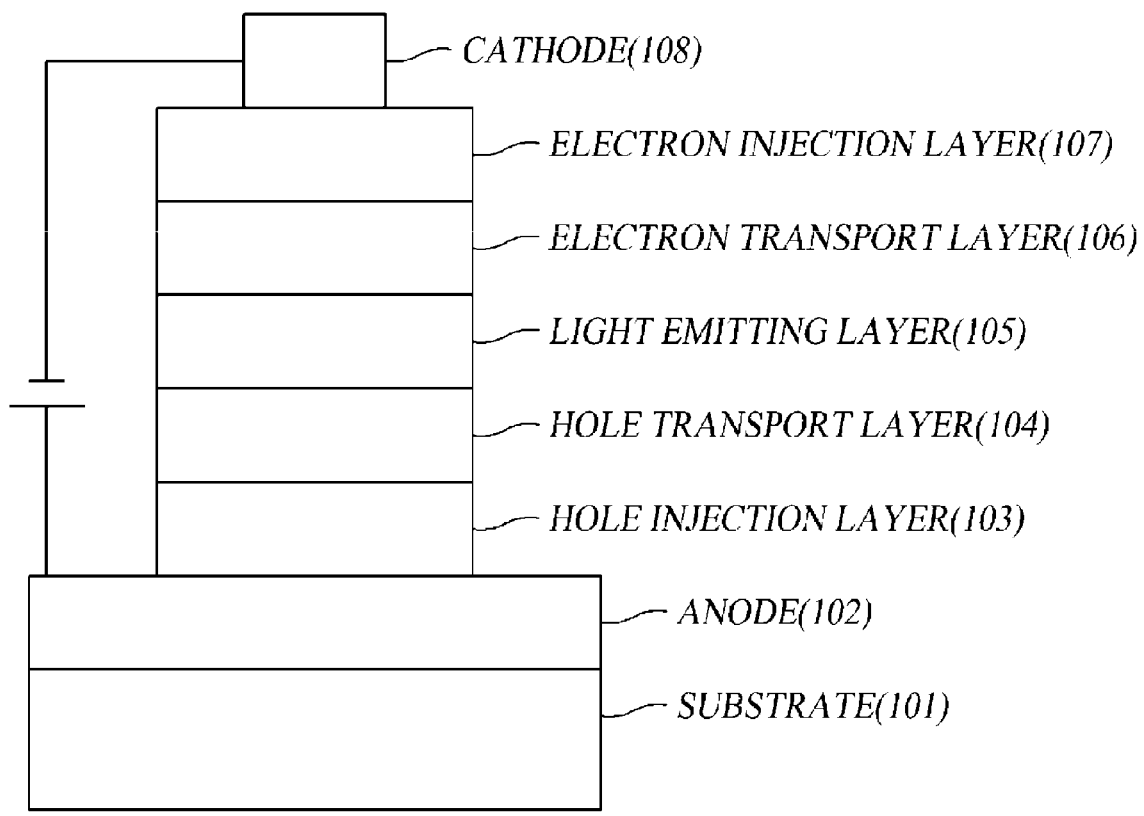
FIGS. 1 to 6 show examples of an organic light emitting diode which can employ a compound according to the present invention.

Hereinafter, exemplary embodiments of the present invention will be described in detail with reference to the accompanying drawings. In reference numerals given to components of respective drawings, it should be noticed that same components are designated by the same reference numerals as far as possible although they are illustrated in different drawings. Further, in the following description of the present invention, a detailed description of known functions and configurations incorporated herein will be omitted when it may make the subject matter of the present invention rather unclear.

In addition, terms, such as first, second, A, B, (a), (b) or the like may be used herein when describing components of the present invention. Each of these terminologies is not used to define an essence, order or sequence of a corresponding component but used merely to distinguish the corresponding component from other component(s). It should be noted that if it is described in the specification that one component is "connected," "coupled" or "joined" to another component, a third component may be "connected," "coupled," and "joined" between the first and second components, although the first component may be directly connected, coupled or joined to the second component.

The present invention provides a compound represented by Formula 1 below.

[Formula 1]

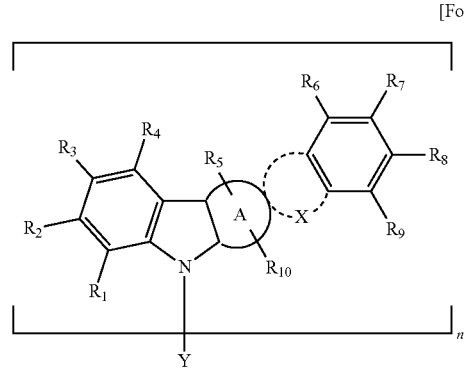

(1) $R_1$ through $R_{10}$ each are independently selected from the group consisting of a hydrogen atom, a halogen atom, a cyano group, an alkoxy group, a thiol group, a substituted or unsubstituted alkyl group having 1 to 50 carbon atoms, a substituted or unsubstituted alkoxy group having 1 to 50 carbon atoms, a substituted or unsubstituted alkenyl group having 1 to 50 carbon atoms, a substituted or unsubstituted arylene group having 5 to 60 carbon atoms, a substituted or unsubstituted aryl group having 5 to 60 carbon atoms, a substituted or unsubstituted aryloxy group having 5 to 60 carbon atoms, a substituted or unsubstituted $C_1$~$C_{50}$ alkyl group having at least one of sulfur (S), nitrogen (N), oxygen (O), phosphorous (P) and silicon (Si), a substituted or unsubstituted $C_5$~$C_{60}$ heteroaryl group having at least one of sulfur (S), nitrogen (N), oxygen (O), phosphorous (P) and silicon (Si), and a substituted or unsubstituted $C_5$~$C_{60}$ heteroaryloxy group having at least one of sulfur, nitrogen, oxygen, phosphorous and silicon.

(2) $R_1$ through $R_{10}$ each may form a substituted or unsubstituted saturated or unsaturated ring together with an adjacent group.

(3) X is at least one selected from sulfur, oxygen or silicon.

(4) Y is selected from the group consisting of a hydrogen atom, a halogen atom, a cyano group, an alkoxy group, a thiol group, a substituted or unsubstituted alkyl group having 1 to 50 carbon atoms, a substituted or unsubstituted alkenyl group having 1 to 50 carbon atoms, a substituted or unsubstituted arylene group having 5 to 60 carbon atoms, a substituted or unsubstituted aryl group having 5 to 60 carbon atoms, a substituted or unsubstituted aryloxy group having 5 to 60 carbon atoms, a substituted or unsubstituted $C_1$~$C_{50}$ alkyl group having at least one of sulfur, nitrogen, oxygen, phosphorous and silicon, a substituted or unsubstituted $C_5$~$C_{60}$ heteroaryl group having at least one of sulfur, nitrogen, oxygen, phosphorous and silicon, and a substituted or unsubstituted $C_5$~$C_{60}$ heteroaryloxy group having at least one of sulfur, nitrogen; oxygen, phosphorous and silicon.

(5) n is an integer from 1 to 3.

(6) the compound having the structural formula above may be used for a soluble process.

Formula 1 may be represented by Formulas 2 to 7 below according to preparation and synthesis methods.

[Formula 2]

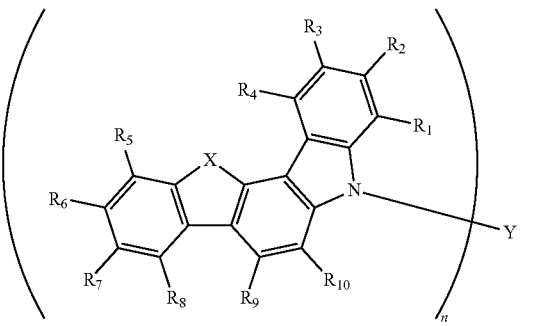

[Formula 3]

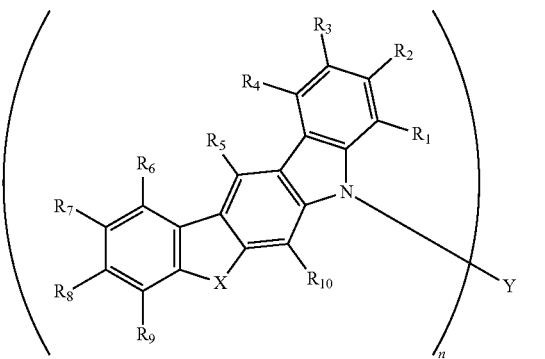

[Formula 4]

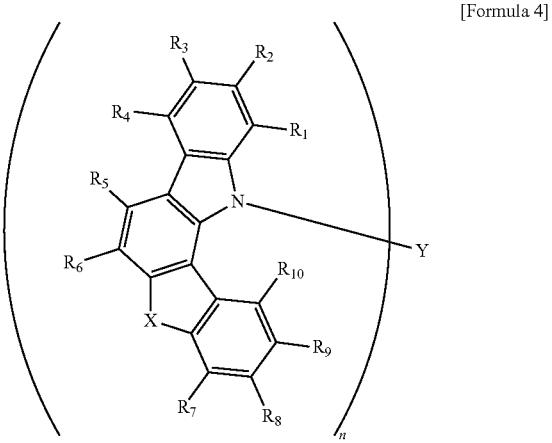

[Formula 5]
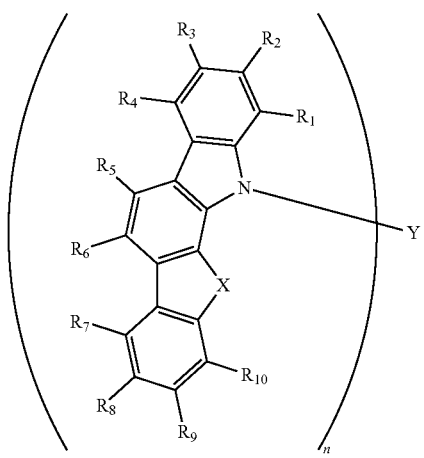
[Formula 6]
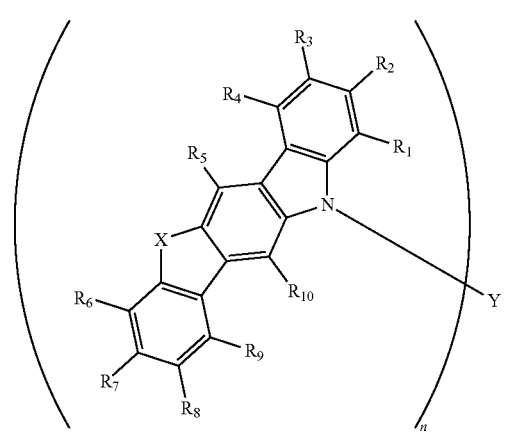
[Formula 7]
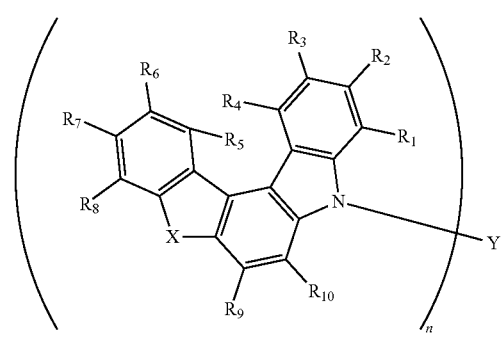
Formula 2 above may be represented by Formula 8 below.
[Formula 8]
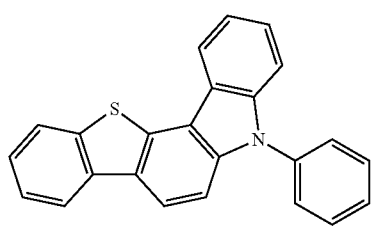
1-1
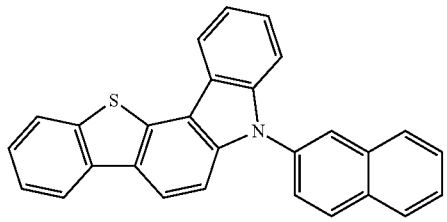
1-2
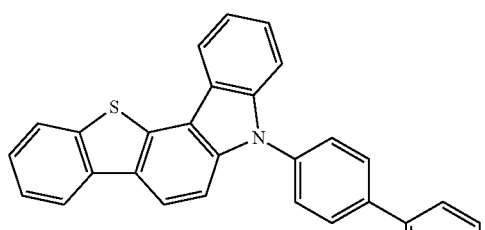
1-3
1-4
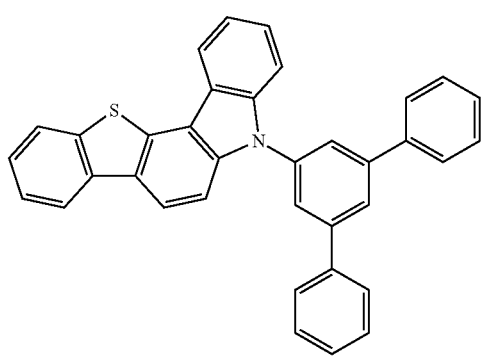
1-5
1-6
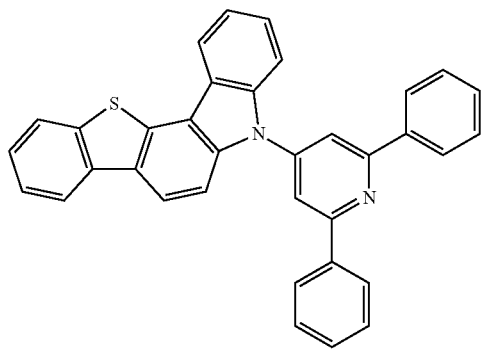

1-7
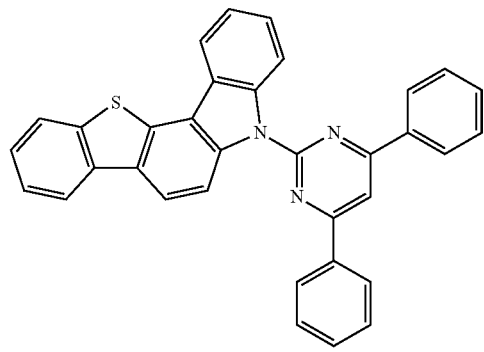
1-8
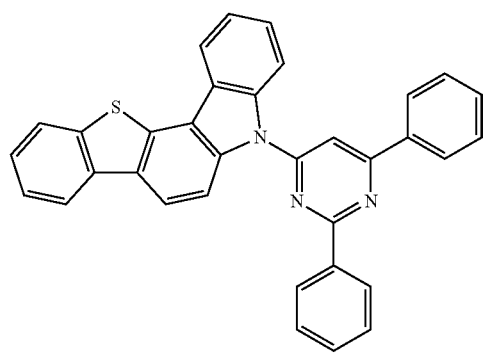
1-9
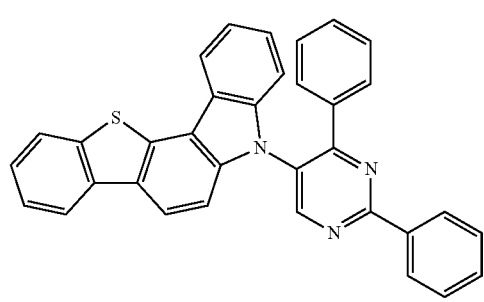
1-10
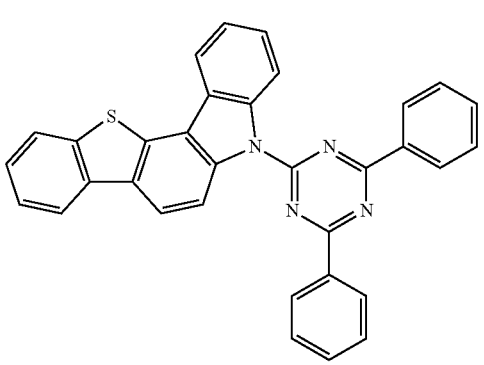
1-11
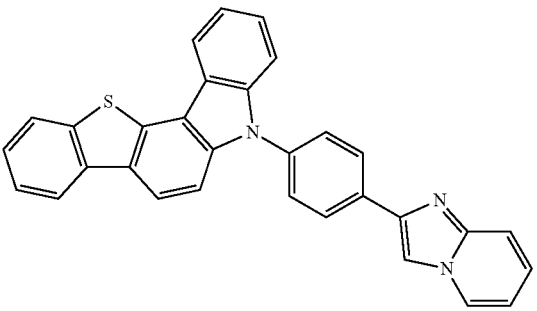
1-12
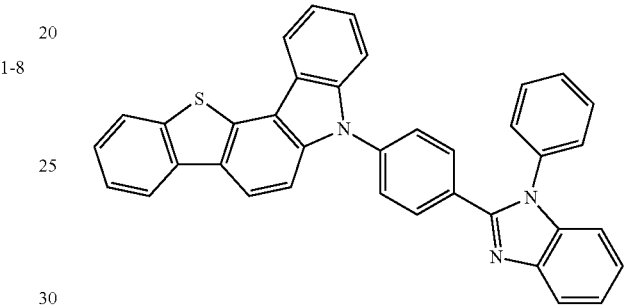
1-13
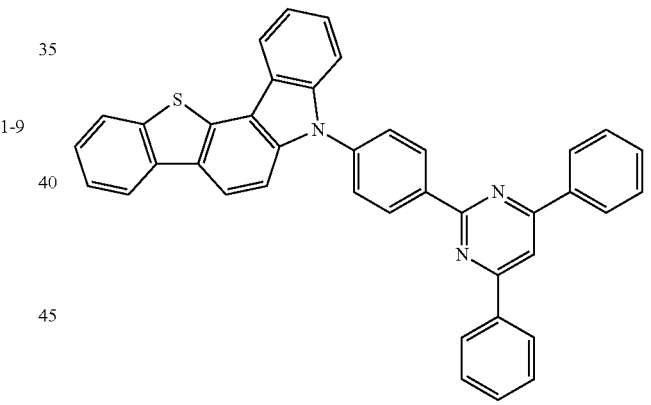
1-14
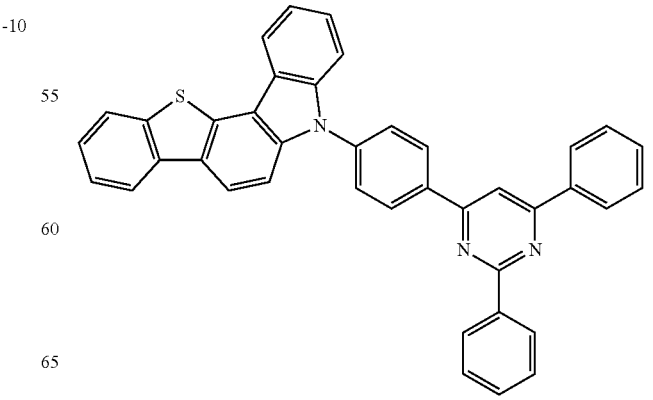

-continued
1-15
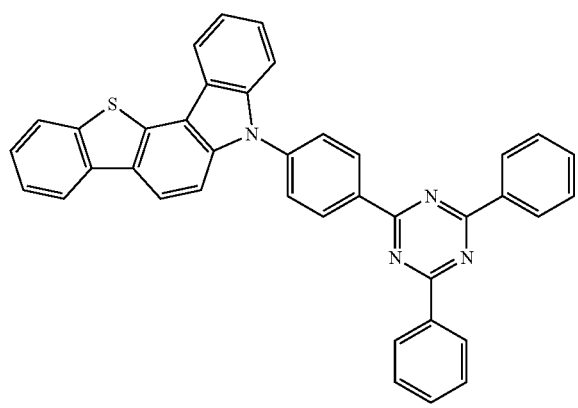
1-16
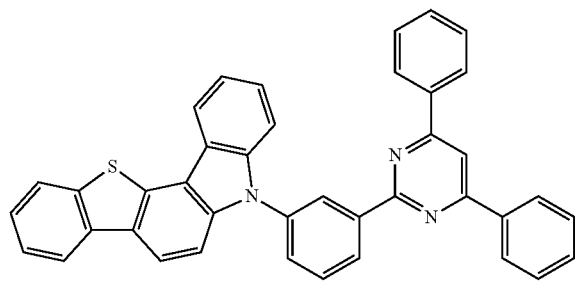
1-17
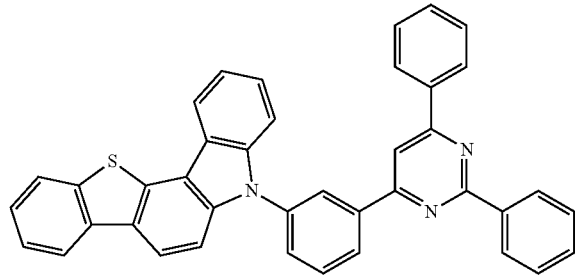
1-18
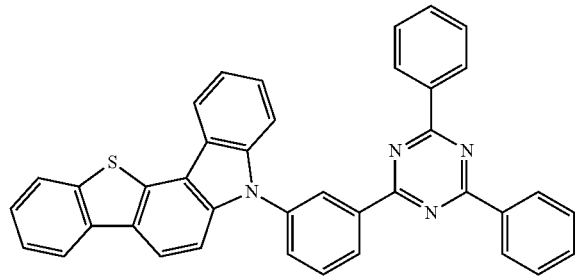
-continued
1-19
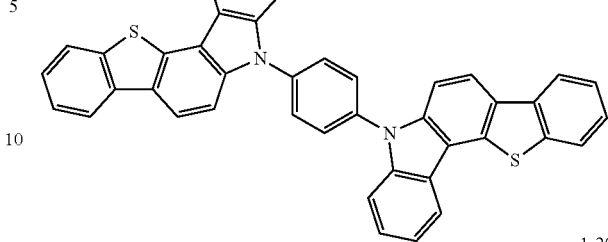
1-20
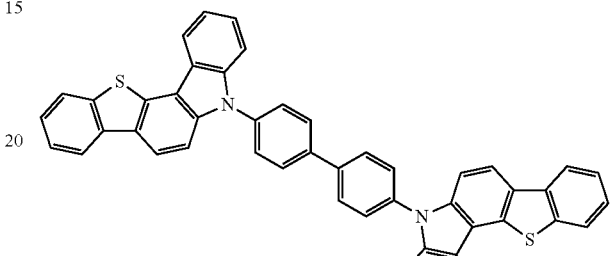
1-21
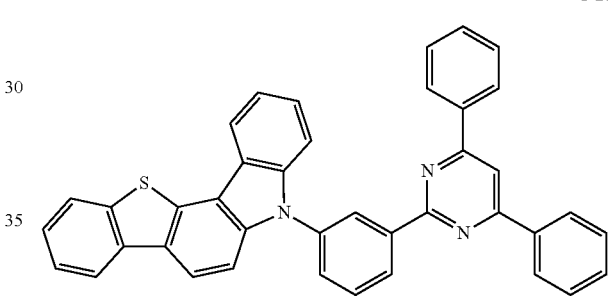
1-22
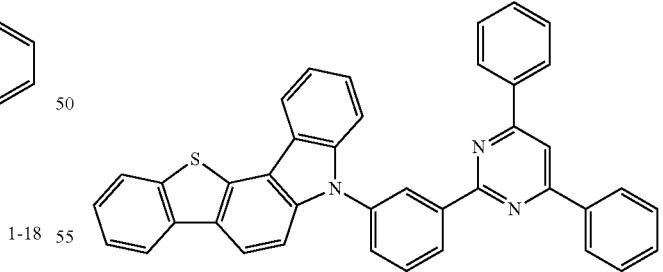
Formula 3 above may be represented by Formula 9 below.

[Formula 9]
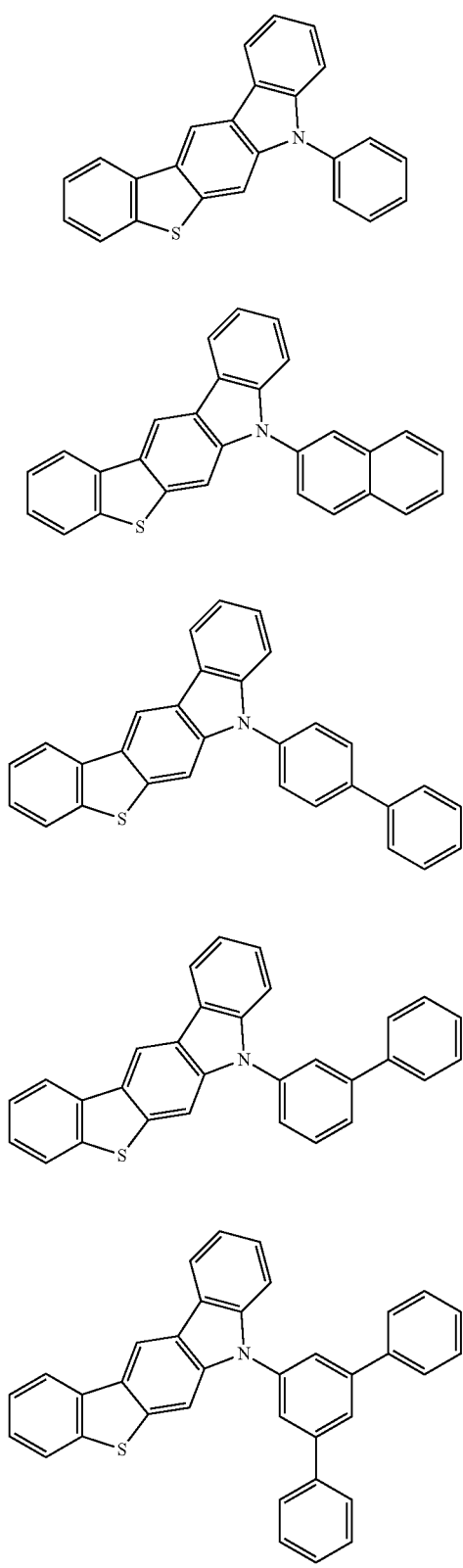
2-1
2-2
2-3
2-4
2-5
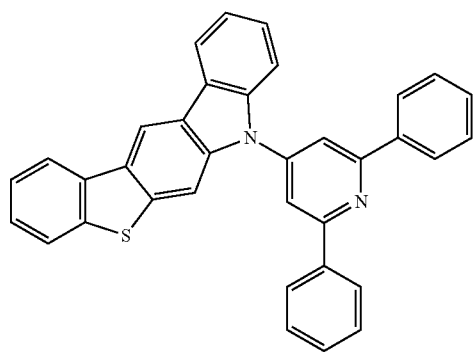
2-6
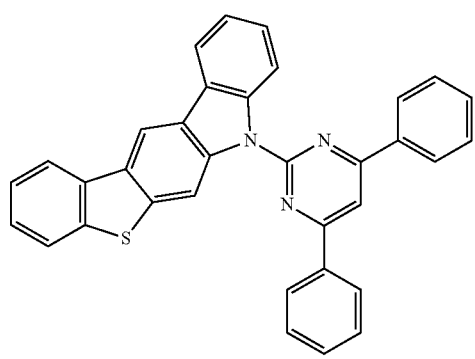
2-7
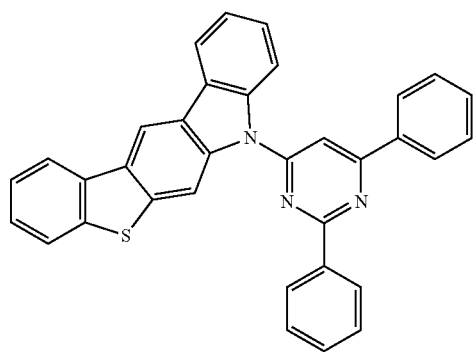
2-8
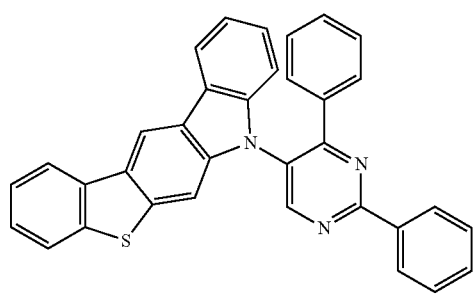
2-9

2-10
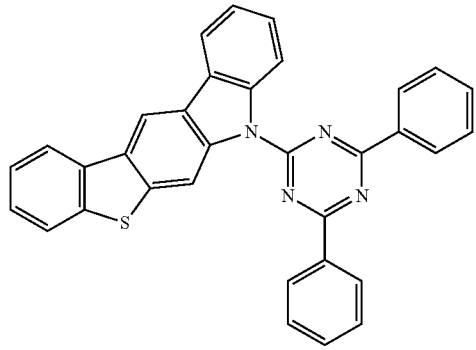
2-11
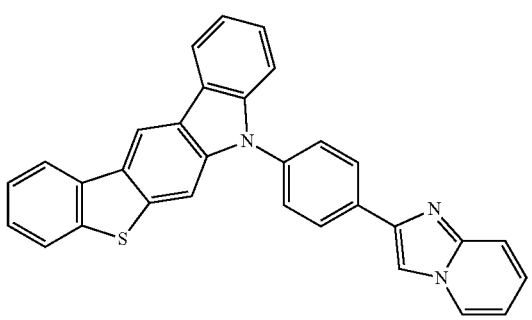
2-12
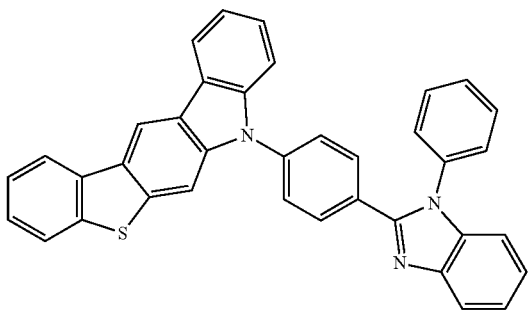
2-13
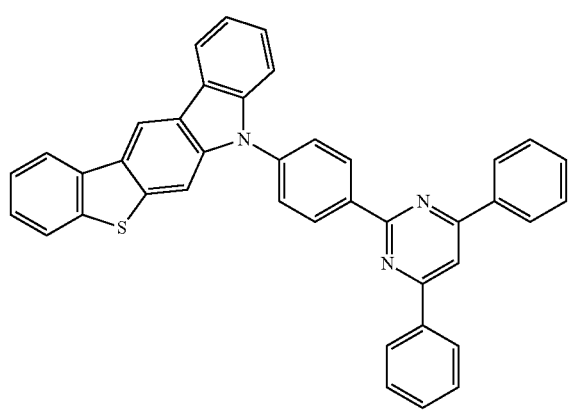
2-14
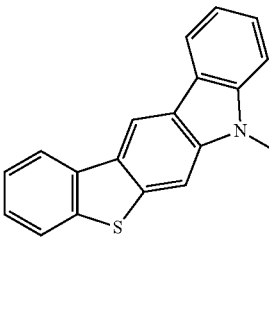
2-15
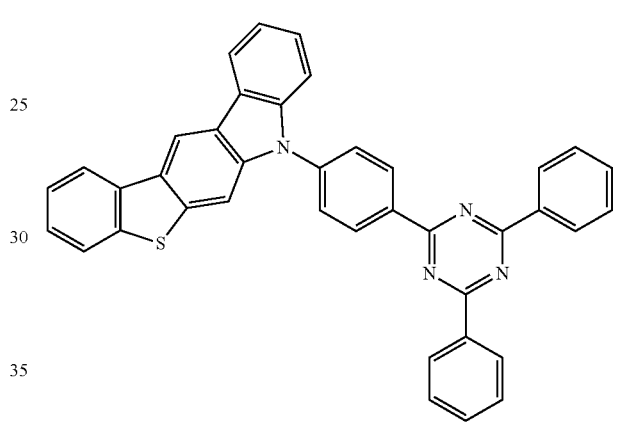
2-16
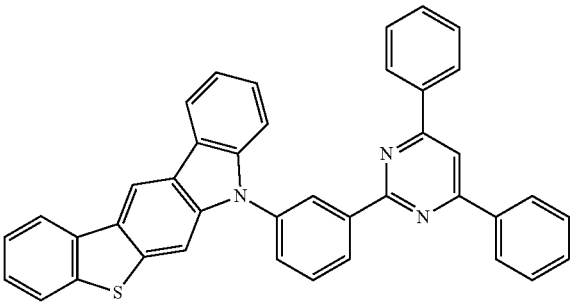
2-17
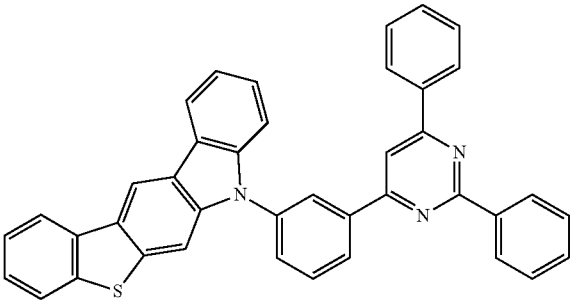

2-18
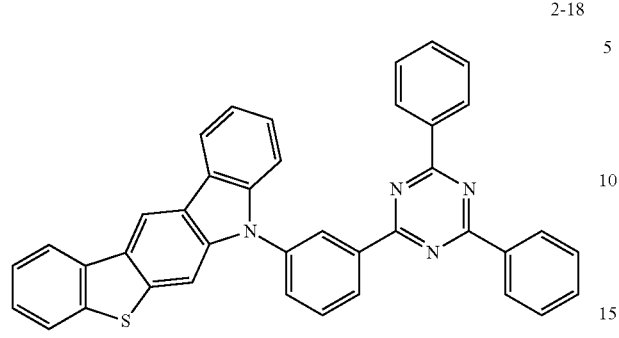
2-19
2-20
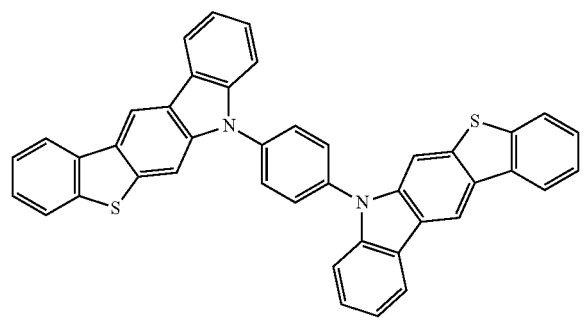
2-21
2-22
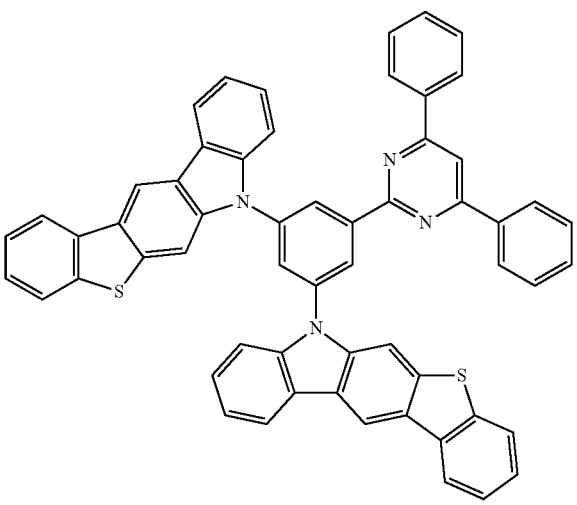
Formula 4 above may be represented by Formula 10 below.
[Formula 10]
3-1
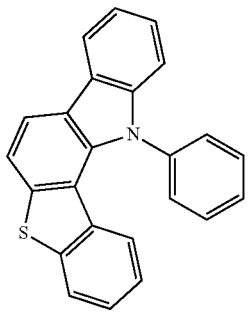
3-2
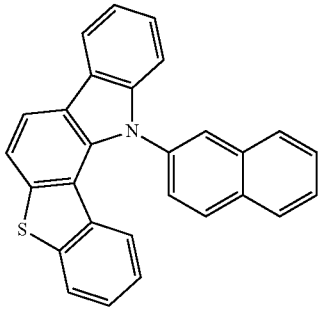
3-3
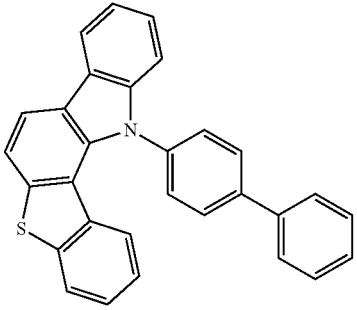

3-4
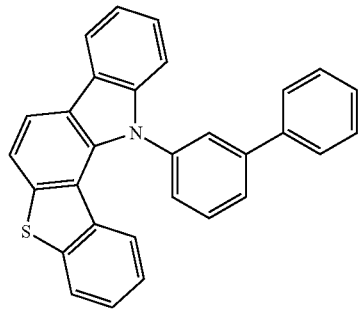
3-5
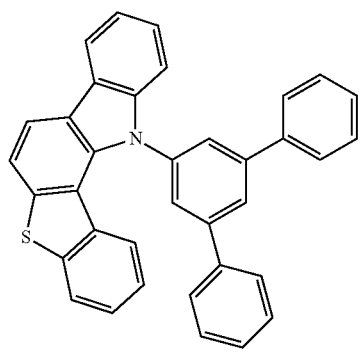
3-6
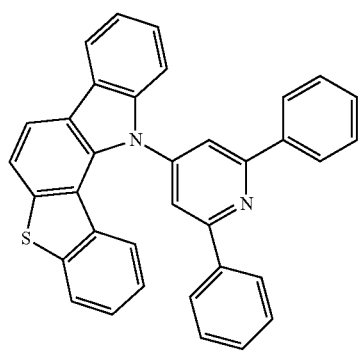
3-7
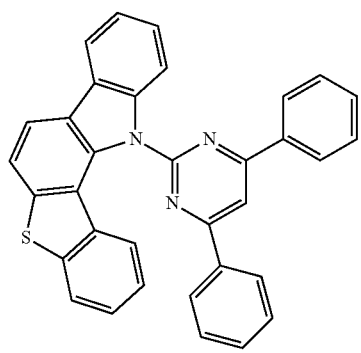
3-8
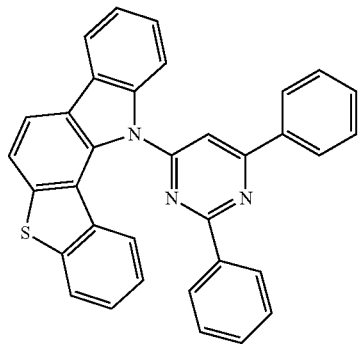
3-9
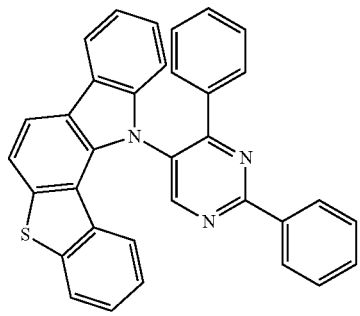
3-10
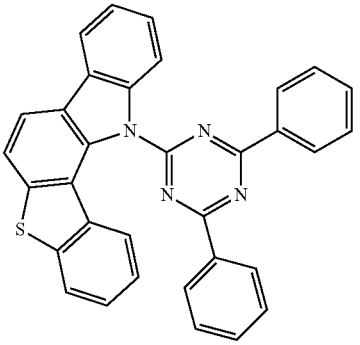
3-11
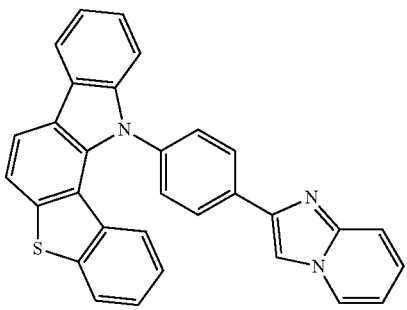
3-12
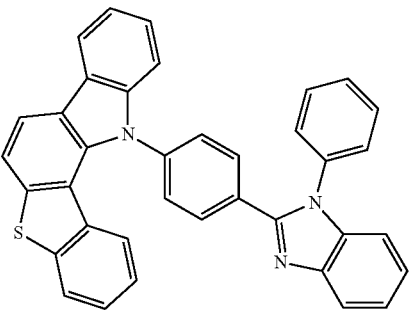

3-13
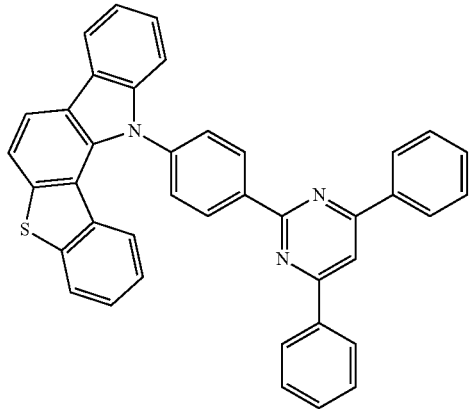
3-14
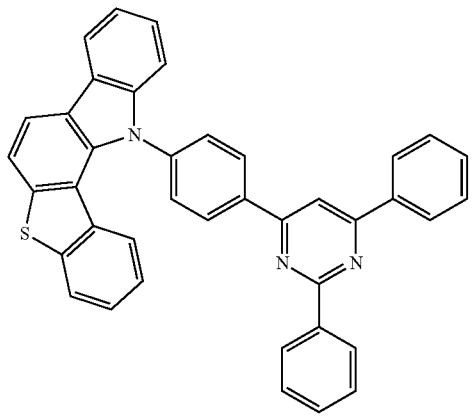
3-15
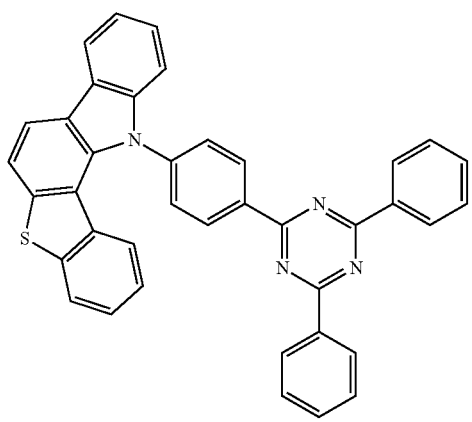
3-16
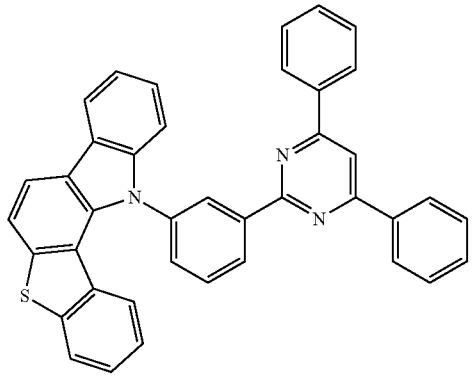
3-17
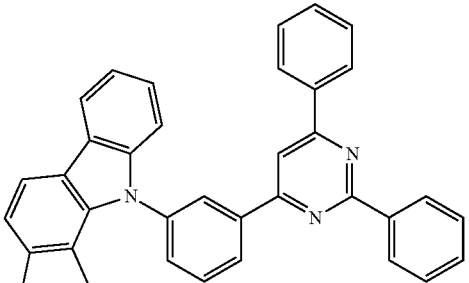
3-18
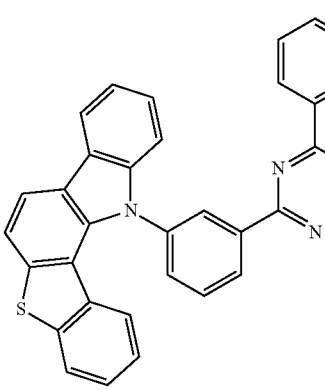
3-19
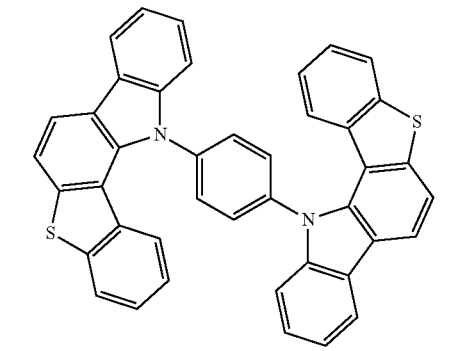
3-20
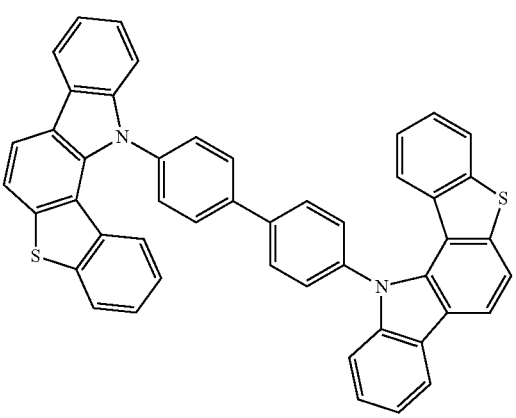

3-21
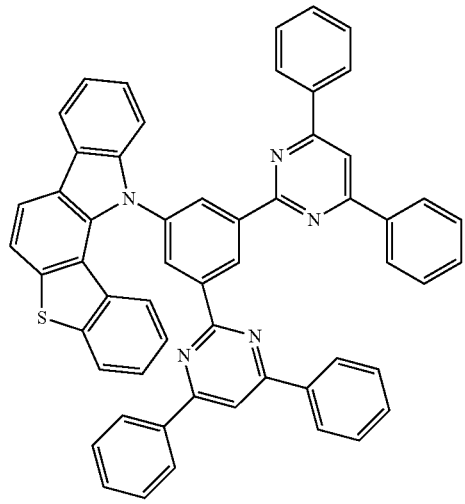
3-22
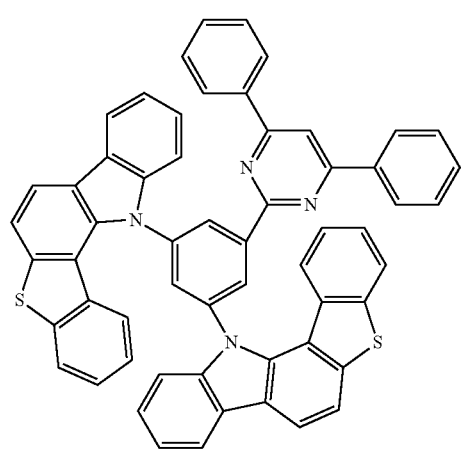
Formula 5 above may be represented by Formula 11 below.
[Formula 11]
4-1
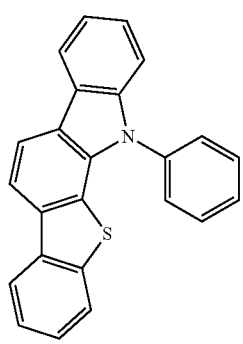
4-2
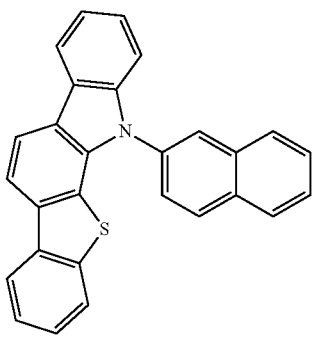
4-3
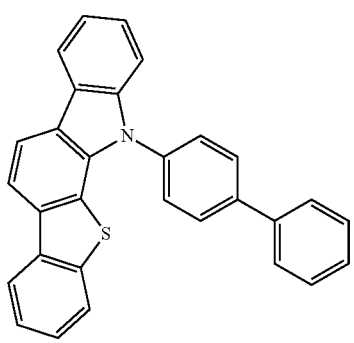
4-4
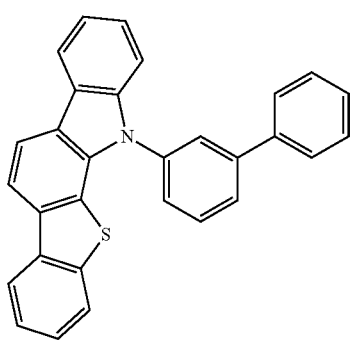
4-5
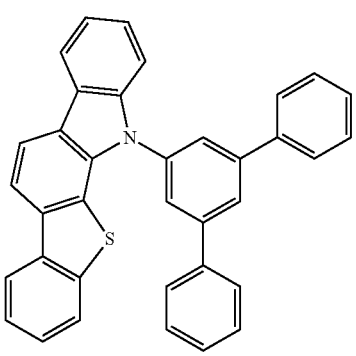

4-6
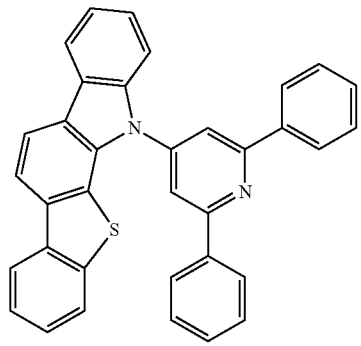
4-7
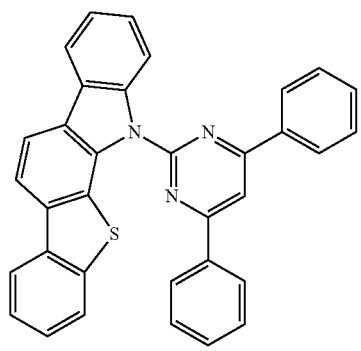
4-8
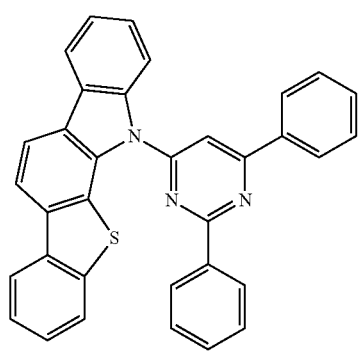
4-9
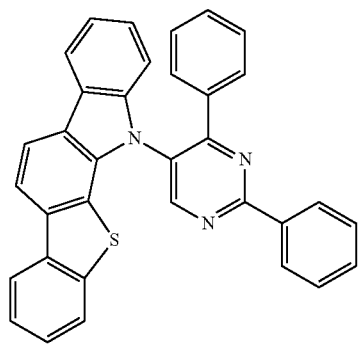
4-10
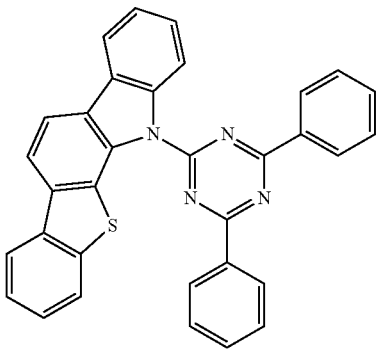
4-11
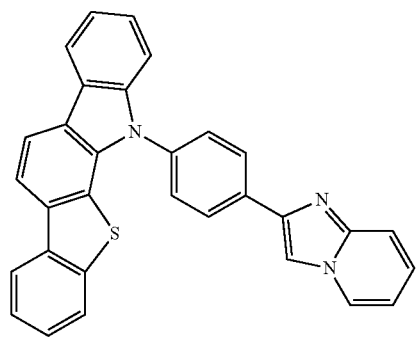
4-12
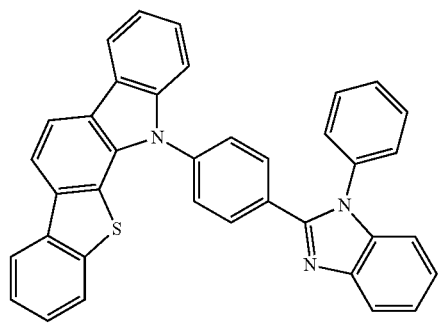
4-13
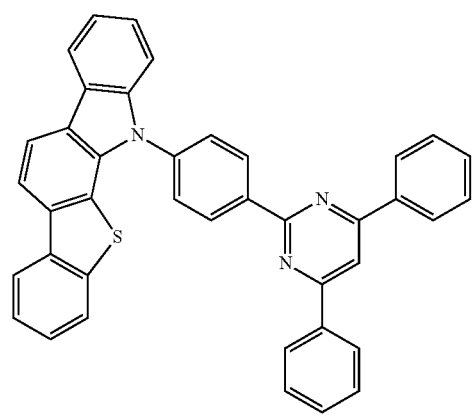

4-14
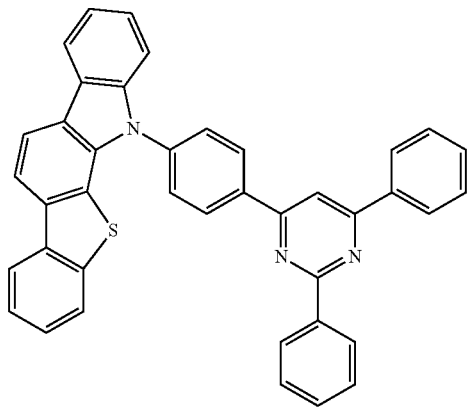
4-15
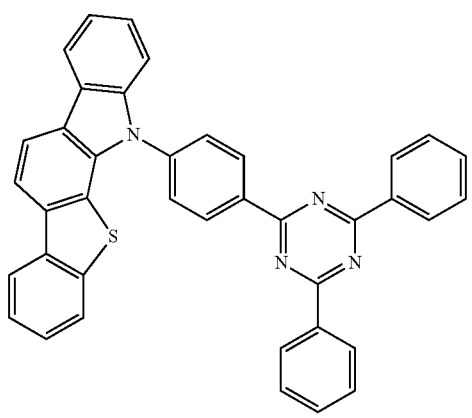
4-16
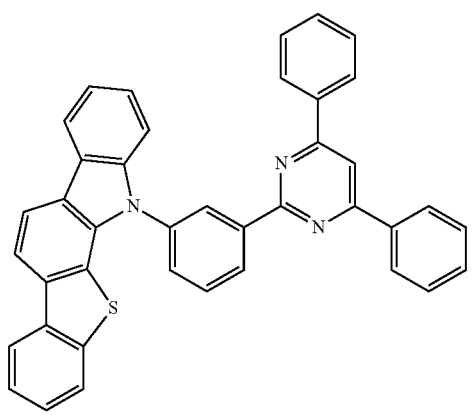
4-17
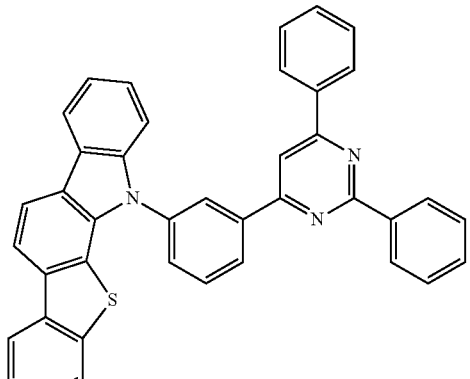
4-18
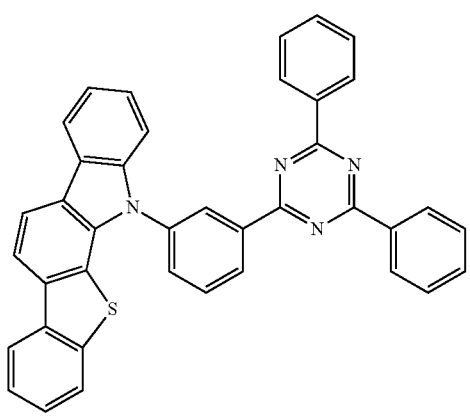
4-19
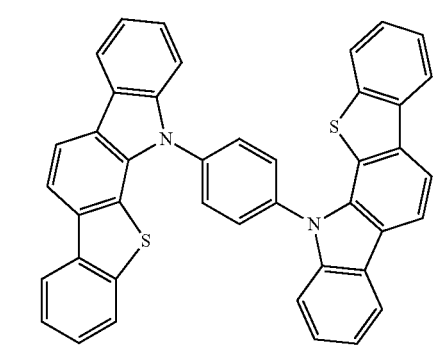
4-20
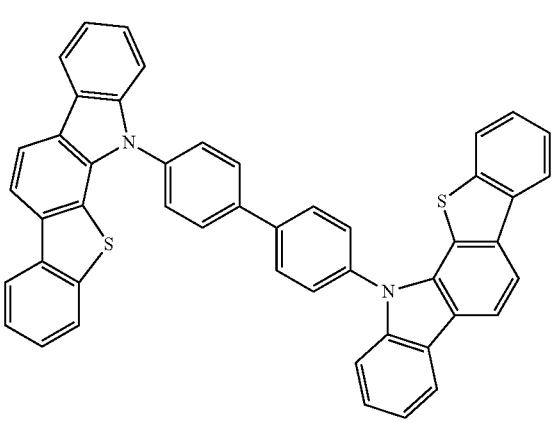

4-21
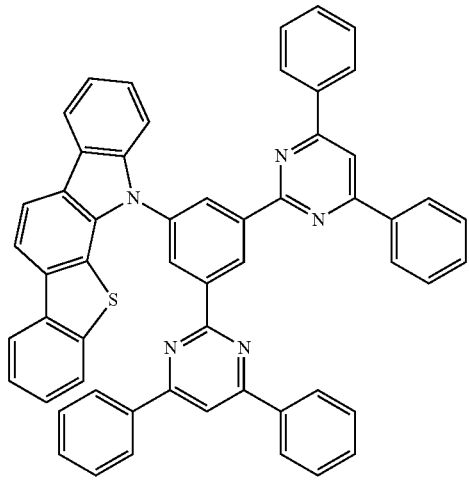
4-22
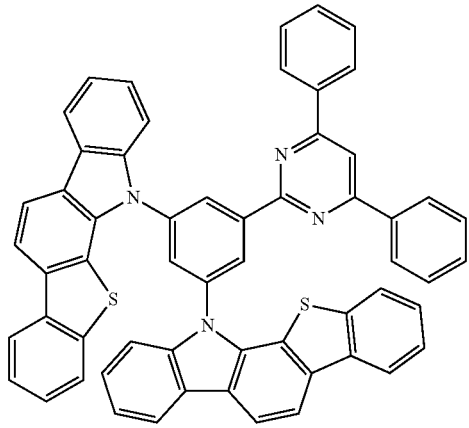
Formula 6 above may be represented by Formula 12 below.
[Formula 12]
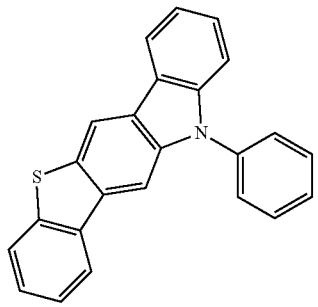
5-1
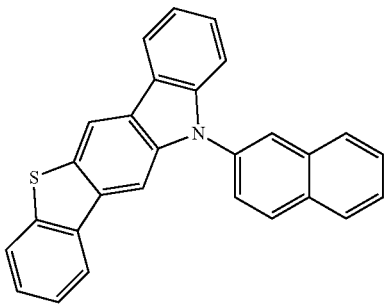
5-2
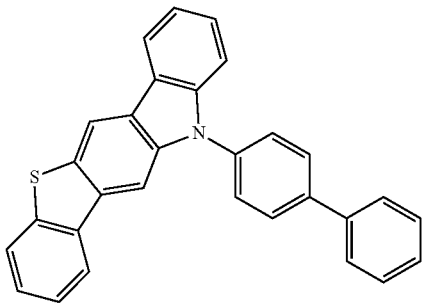
5-3
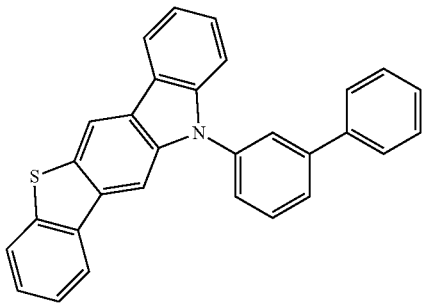
5-4
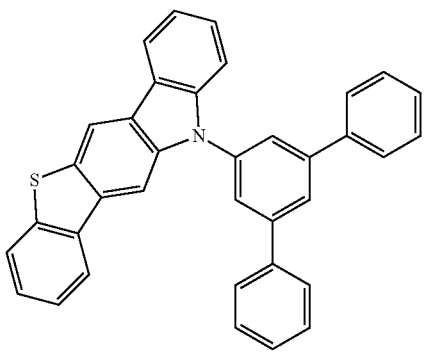
5-5
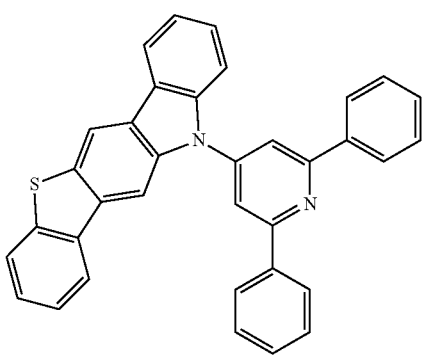
5-6

-continued
5-7
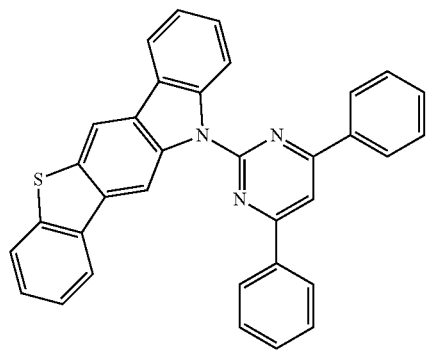
5-8
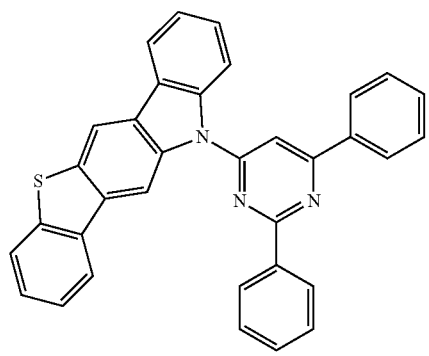
5-9
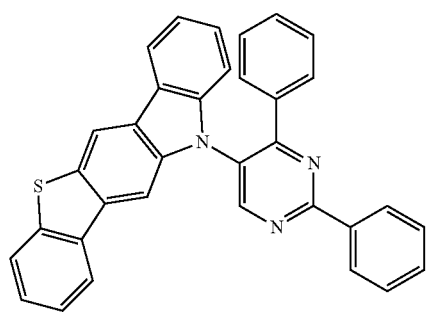
5-10
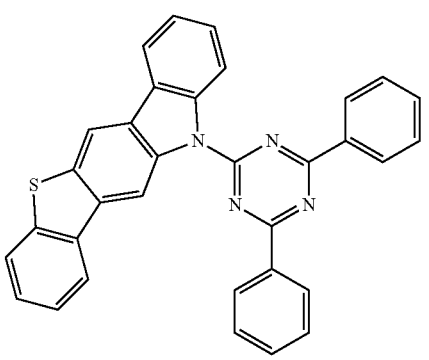
-continued
5-11
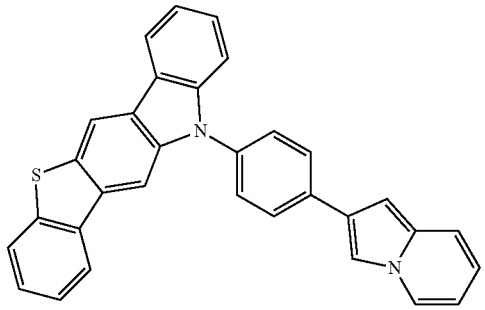
5-12
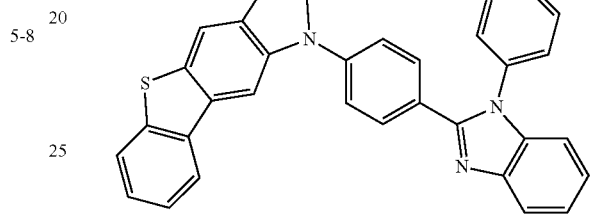
5-13
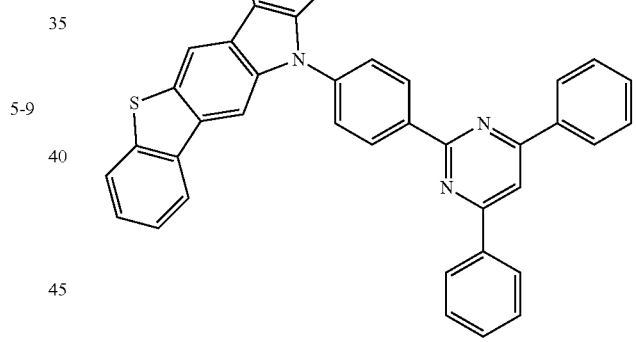
5-14
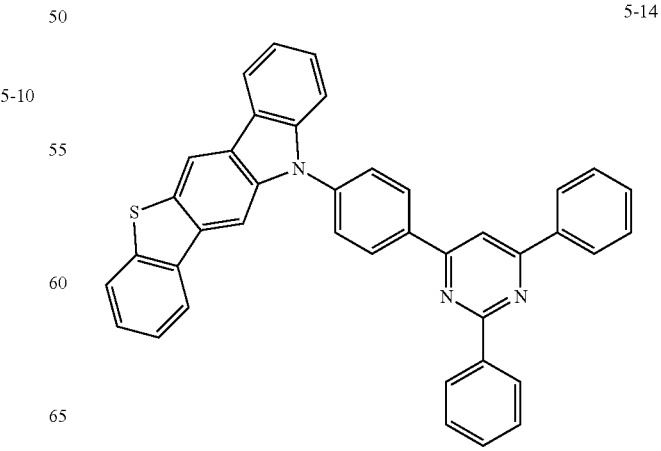

5-15
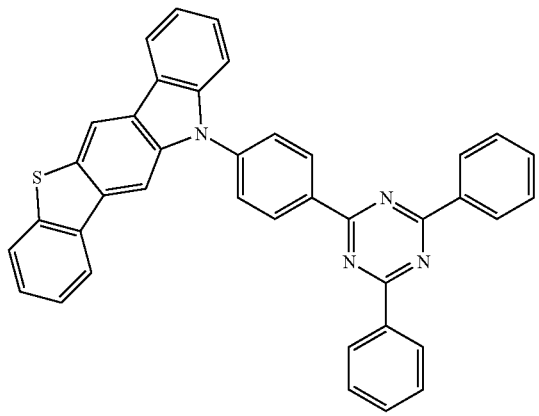
5-16
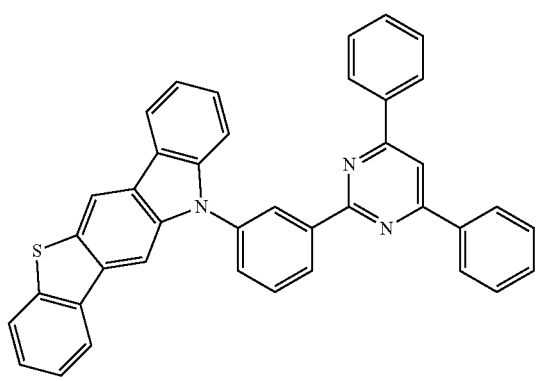
5-17
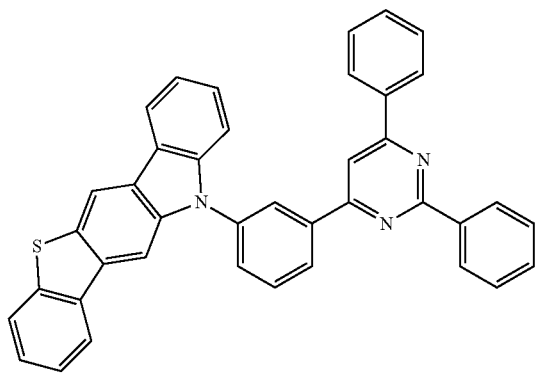
5-18
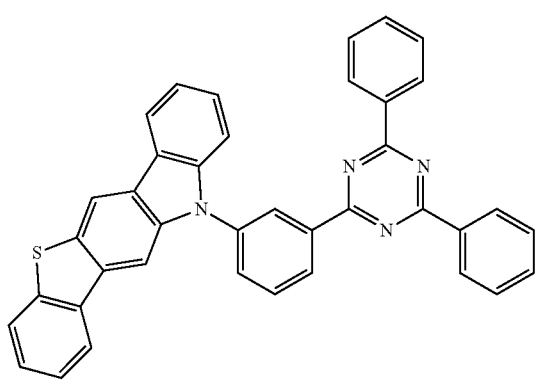
5-19
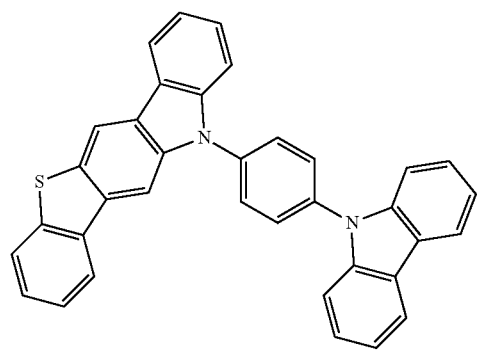
5-20
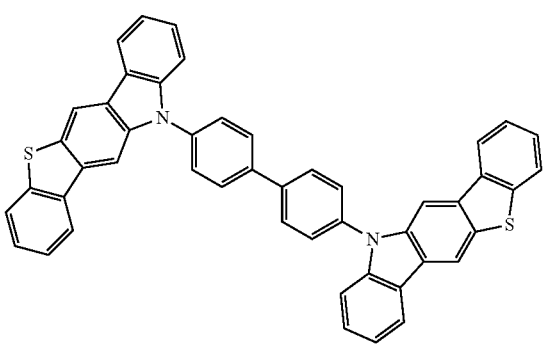
5-21
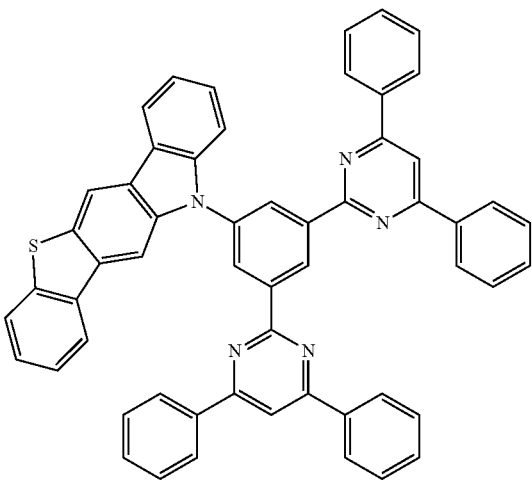

5-22
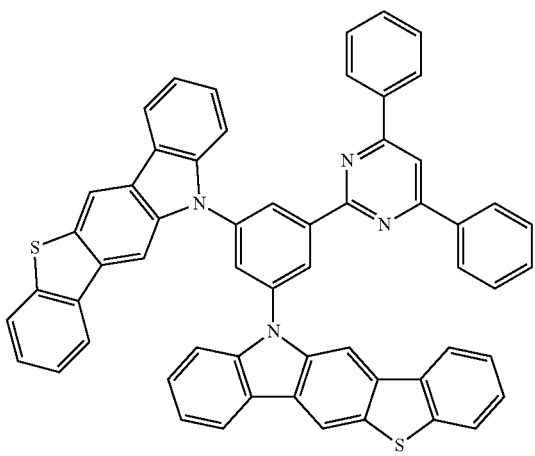
6-5
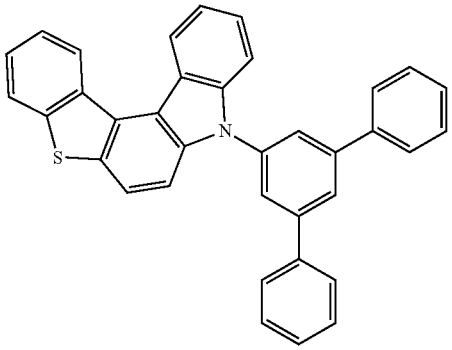
Formula 7 above may be represented by Formula 13 below.
[Formula 13]
6-1
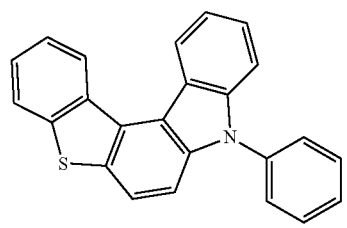
6-6
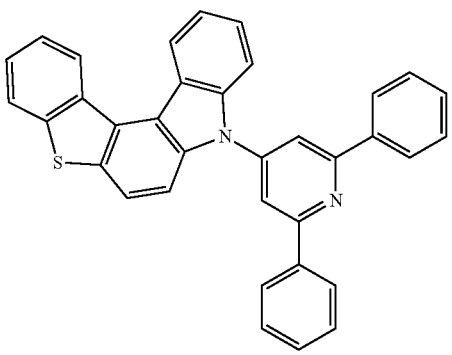
6-2
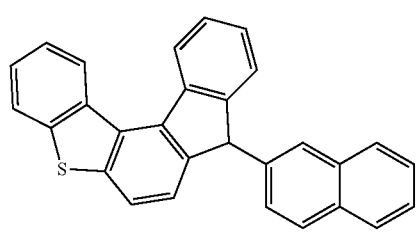
6-3
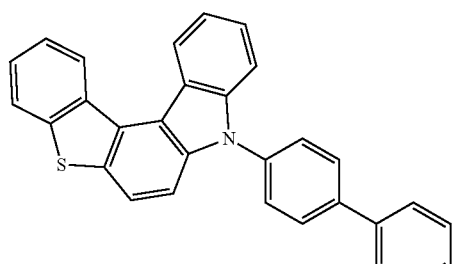
6-7
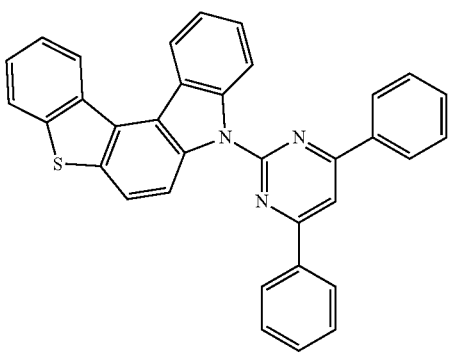
6-4
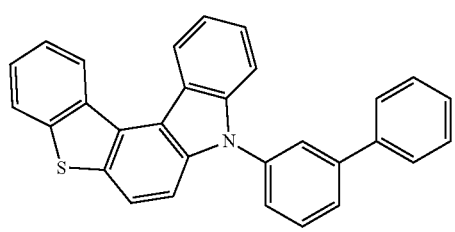
6-8
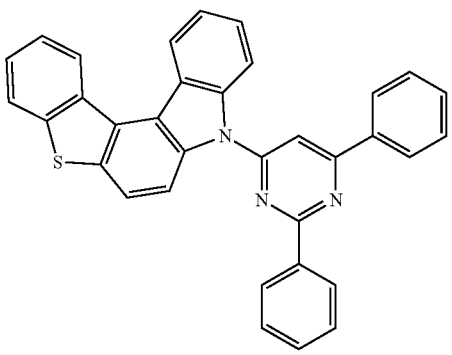

6-9
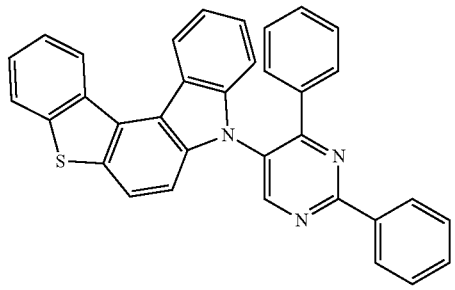
6-10
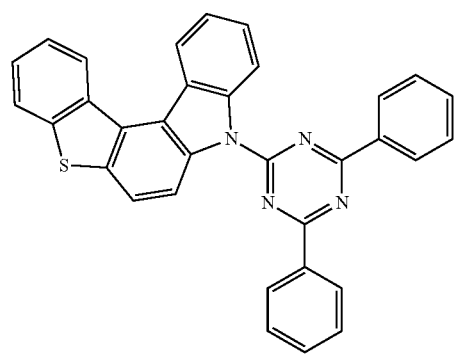
6-11
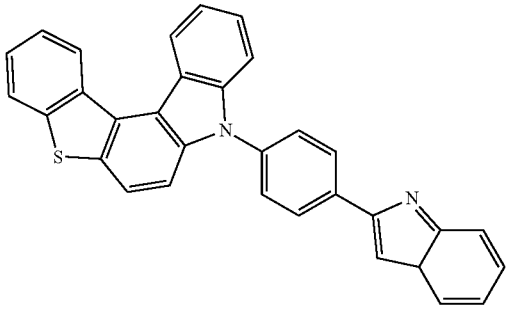
6-12
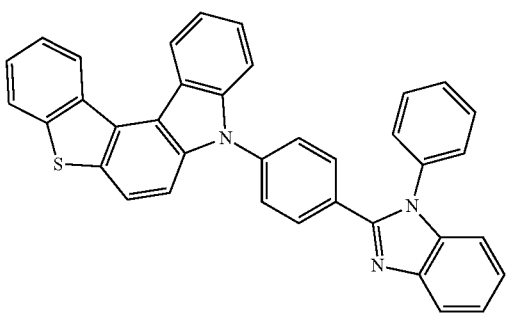
6-13
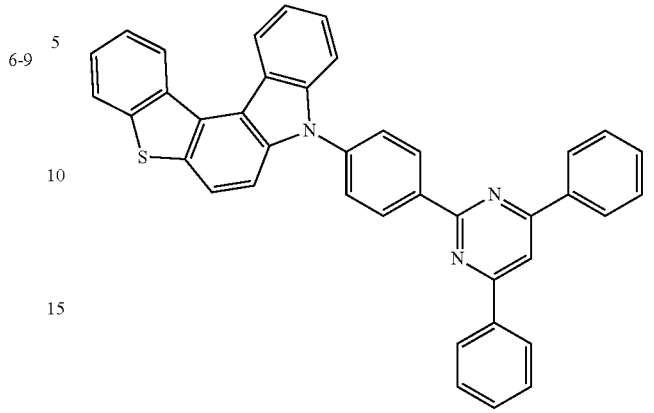
6-14
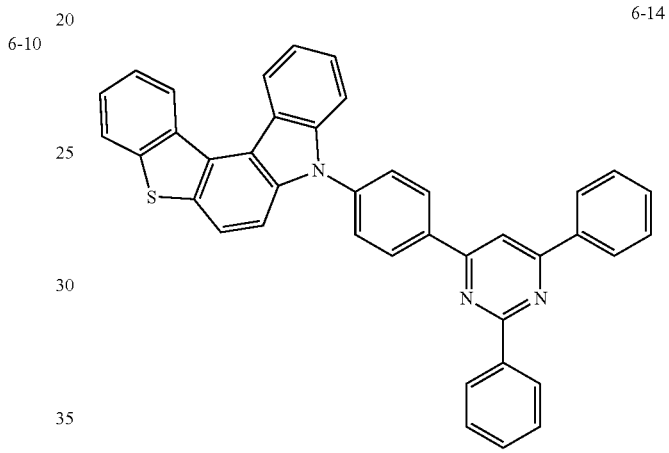
6-15
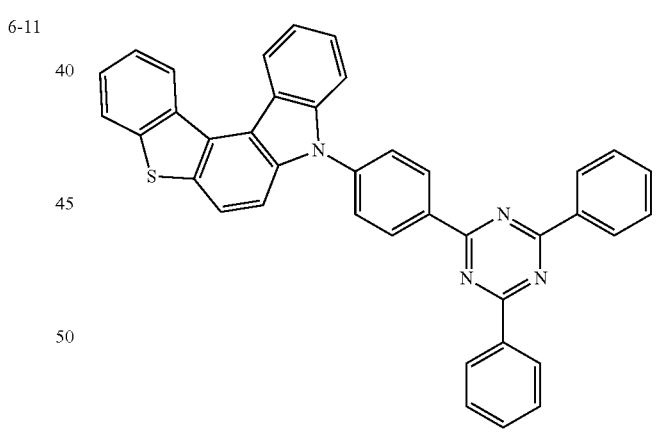
6-16
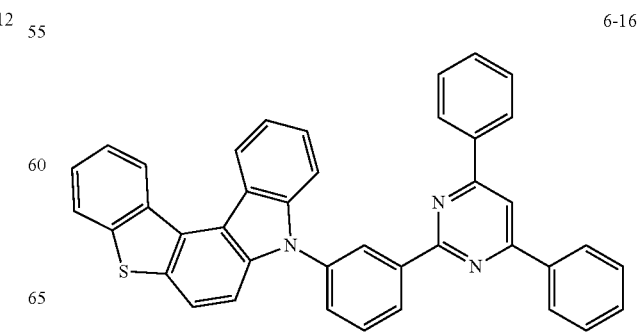

6-17
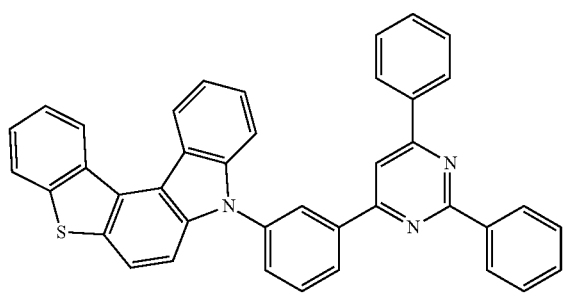

6-18
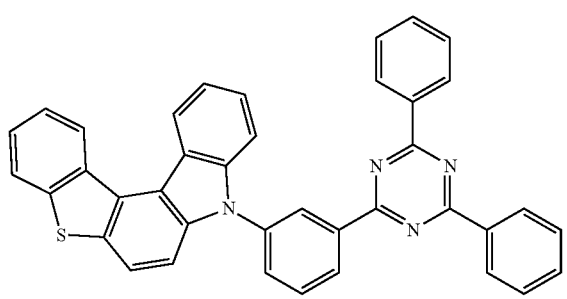

6-19
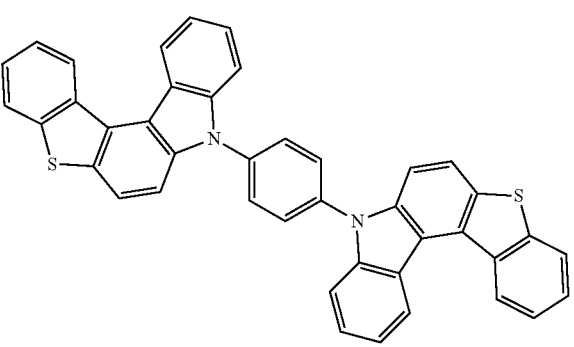

6-20
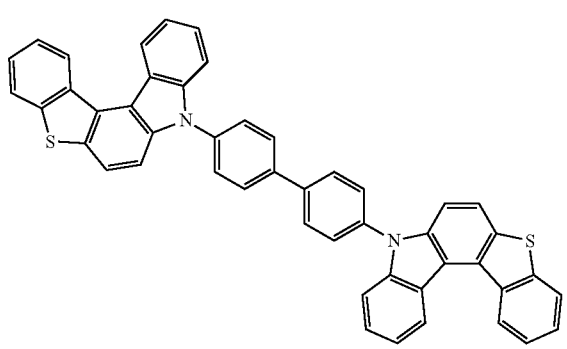

6-21
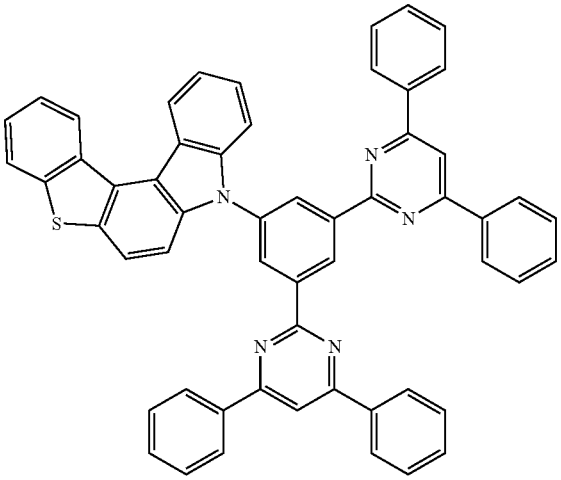

6-22
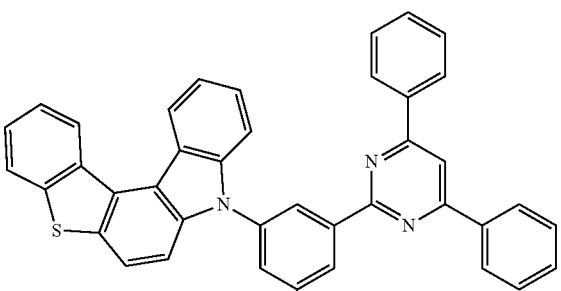
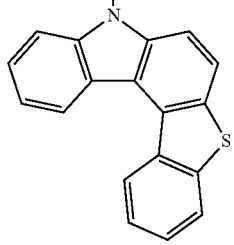

According to one embodiment of the present invention, specific examples of a compound including a 5-membered heterocycle, represented by Formula 1 may include compounds represented by Formulas 2 to 7, and further may be represented by Formulas 8 to 13. However, the present invention is not limited thereto.

There exist various organic electronic devices which employ compounds including a 5-membered heterocycle, as described with reference to Formulas 1 to 13, as an organic material layer. The organic electronic devices in which compounds including a 5-membered heterocycle, as described with reference to Formulas 1 to 13, can be employed, may include, for example, an organic light emitting diode (OLED), an organic solar cell, an organic photo conductor (OPC) drum, an organic transistor (organic TFT), and the like.

As one example of the organic electronic devices in which compounds including a 5-membered heterocycle, as described with reference to Formulas 1 to 13, can be used, an organic light emitting diode (OLED) will be described below, but the present invention is not limited thereto. The above described compound including a 5-membered heterocycle may be applied to various organic electronic devices.

In another embodiment of the present invention, there is provided an OLED including a first electrode, a second electrode, and an organic material layer interposed between these electrodes, in which at least one of organic material layers includes the compounds represented by Formulas 1 to 13.

Figure 2:
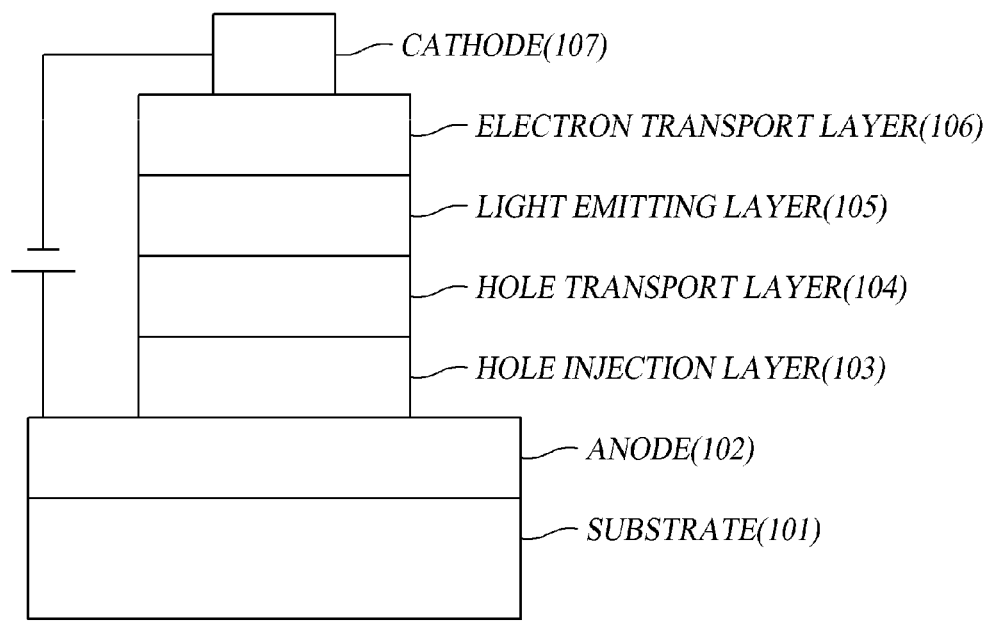
Figure 3:
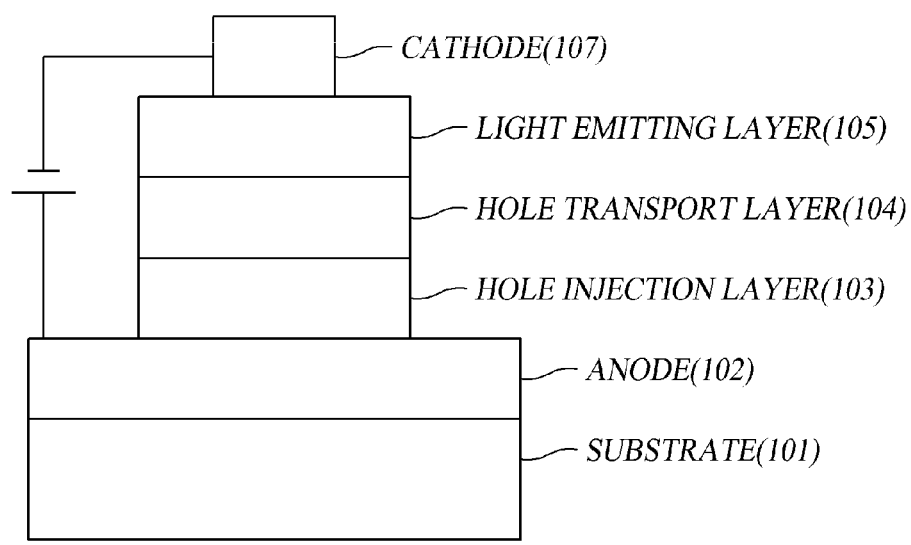
Figure 4:
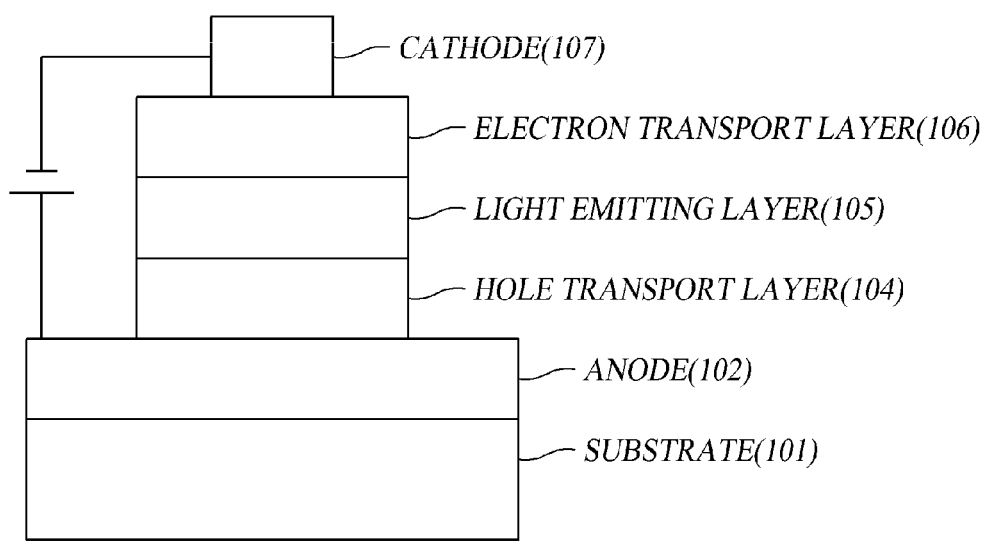
Figure 5:
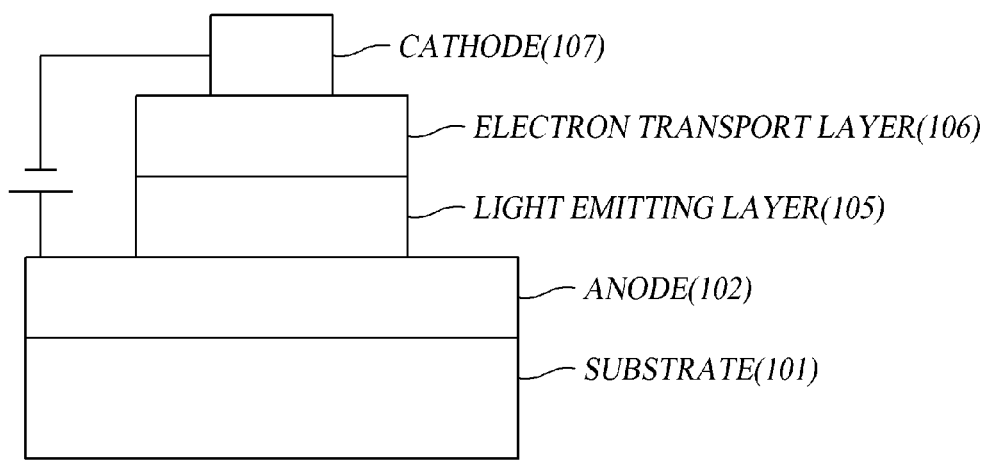
Figure 6:
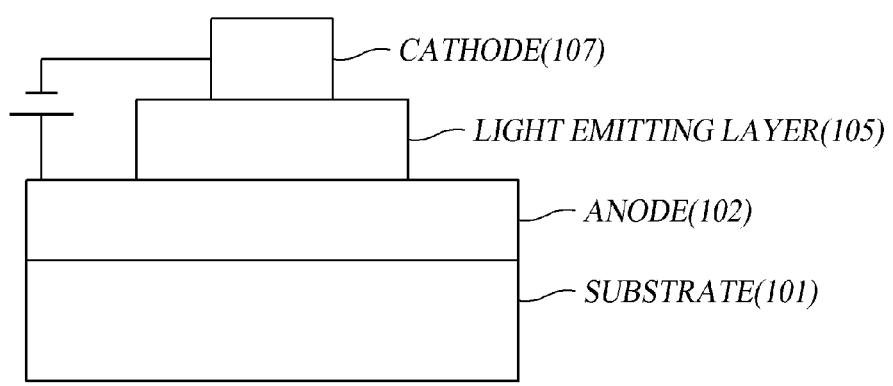

FIGS. 1 to 6 show examples of an OLED which can employ a compound according to the present invention.

The OLED according to another embodiment of the present invention may be manufactured by means of a manufacturing method and materials conventionally known in the art in such a manner that it can have a conventionally known structure, except that at least one of organic material layers including a hole injection layer, a hole transport layer, a light emitting layer, an electron transport layer, and an electron injection layer is formed in such a manner that it can include the compounds represented by Formulas 1 to 13.

The structures of the OLED according to another embodiment of the present invention are shown in FIGS. 1 to 6, but the present invention is not limited to the structures. Herein, in the embodiment shown in FIG. 1, the reference numeral 101 indicates a substrate, 102 indicates an anode, 103 indicates a hole injection layer (HIL), 104 indicates a hole transport layer (HTL), 105 indicates a light emitting layer (EML), 106 indicates an electron injection layer (EIL), 107 indicates an electron transport layer (ETL), and 108 indicates a cathode. Although not shown, such an OLED may further include a hole blocking layer (HBL) for blocking movement of holes, an electron blocking layer (EBL) for blocking movement of electrons, and a protective layer. The protective layer may be formed in such a manner that it, as an uppermost layer, can protect an organic material layer or a cathode.

Herein, the compound including a 5-membered heterocycle, as described with reference to Formulas 1 to 13, may be included in at least one of organic material layers including a hole injection layer, a hole transport layer, a light emitting layer, and an electron transport layer. Specifically, the compound including a 5-membered heterocycle, as described with reference to Formulas 1 to 13, may be substituted for at least one of a hole injection layer, a hole transport layer, a light emitting layer, an electron transport layer, an electron injection layer, a hole blocking layer, an electron blocking layer, and a protective layer, or may be used in combination with these layers. Of course, the compound may be used for not only one layer of the organic material layers but also two or more layers.

Especially, the compound including a 5-membered heterocycle, as described with reference to Formulas 1 to 13, may be used as a material for hole injection, hole transport, electron injection, electron transport, light emission, and passivation (capping). Especially, it may be used alone as a light emitting material, a host or a dopant.

For example, in manufacturing of the OLED according to another embodiment of the present invention, a metal, a conductive metal oxide, or an alloy thereof is deposited on a substrate by means of PVD (physical vapor deposition) such as sputtering or e-beam evaporation so as to form an anode, and then an organic material layer including a hole injection layer, a hole transport layer, a light emitting layer, an electron transport layer, and an electron injection layer is formed thereon, and a material used as a cathode is deposited thereon.

Besides, on a substrate, a cathode material, an organic material layer, and an anode material may be sequentially deposited so as to provide an organic electronic device. The organic material layer may be formed in a multi-layered structure including a hole injection layer, a hole transport layer, a light emitting layer, an electron transport layer, and an electron injection layer, but the present invention is not limited thereto. It may be formed in a single layer structure. Further, the organic material layer may be manufactured with a smaller number of layers by using various polymer materials by means of a solvent process (e.g., spin coating, dip coating, doctor blading, screen printing, inkjet printing, or thermal transfer) instead of deposition.

In the OLED according to another embodiment of the present invention, the organic material layer may be formed by a soluble process, such as a spin coating process or an inkjet process, of the above described compound including a 5-membered heterocycle.

The substrate is a support for the OLED, and may employ a silicon wafer, a quartz or glass plate, a metallic plate, a plastic film or sheet.

On the substrate, an anode is positioned. Such an anode allows holes to be injected into a hole injection layer positioned thereon. As an anode material, a material having a high work function is preferably used so that injection of holes into an organic material layer can be smoothly carried out. Specific examples of an anode material used for the present invention may include: metals (such as vanadium, chromium, copper, zinc, gold) or alloys thereof; metallic oxides such as zinc oxide, indium oxide, indium tin oxide (ITO), indium zinc oxide (IZO); a metal-oxide combination such as ZnO:Al or $SnO_2$:Sb; and conductive polymers such as poly(3-methylthiophene), poly[3,4-(ethylene-1,2-dioxy)thiophene](PEDT), polypyrrole and polyaniline, but the present invention is not limited thereto.

On the anode, a hole injection layer is positioned. A material for such a hole injection layer is required to have a high efficiency for injecting holes from an anode, and to be able to efficiently, transport the injected holes. For this, the material has a low ionization potential, a high transparency against visible light, and a high stability for holes.

As a hole injection material, a material into which holes can be well injected from an anode at a low voltage is used. Preferably, HOMO (highest occupied molecular orbital) of the hole injection material ranges from a work function of an anode material to HOMO of adjacent organic material layers. Specific examples of the hole injection material may include metal porphyrine-, oligothiophene-, and arylamine-based organic materials, hexanitrile hexaazatriphenylen- and quinacridone-based organic materials, perylene-based organic materials, and anthraquinone-, polyaniline-, and polythiophene-based conductive polymers, but the present invention is not limited thereto.

On the hole injection layer, hole transport layer is positioned. Such a hole transport layer receives holes transferred from the hole injection layer and transfers them to an organic luminescence layer positioned thereon. Further, the hole transport layer has a high hole mobility and a high hole stability and performs a role of blocking electrons. Besides these general requirements, it requires heat-resistance against a device when applied for car display, and thus is preferably made of a material having a glass transition temperature (Tg) of 70° C. or more. The examples of a material satisfying these conditions may include NPD (or NPB), spiro-arylamine-based compound, perylene-arylamine-based compound, azacycloheptatriene compound, bis(diphenylvinylphenyl)anthracene, silicongermaniumoxide compound, silicon-based arylamine compound, and the like.

On the hole transport layer, an organic luminescence layer is positioned. Such an organic luminescence layer is made of a material having a high quantum efficiency, in which holes and electrons which are injected from an anode and a cathode, respectively, are recombined so as to emit light. As a light emitting material, a material allowing holes and electrons transferred from a hole transport layer and an electron transport layer, respectively, to be combined so as to emit visible light is used. Preferably, a material having a high quantum efficiency against fluorescence or phosphorescence is used.

As a material or a compound satisfying these conditions, for a green color, Alq3 may be used, and for a blue color, Balq(8-hydroxyquinoline beryllium salt), DPVBi(4,4'-bis(2, 2-diphenylethenyl)-1,1'-biphenyl) based, Spiro material, spiro-DPVBi(Spiro-4,4'-bis(2,2-diphenylethenyl)-1,1'-biphenyl), LiPBO(2-(2-benzoxazoyl)-phenol lithium salt), bis (diphenylvinylphenylvinyl)benzene, aluminum-quinoline metal complex, imidazole, thiazol and oxazole-metal complex, or the like may be used. In order to improve the luminous efficiency of a blue color, perylene, and BczVBi(3,3'[(1, 1'-biphenyl)-4,4'-diyldi-2,1-ethenediyl]bis(9-ethyl)-9H-carbazole; DSA(distrylamine)) may be doped in a small amount. For a red color, a green light emitting material may be doped with DCJTB([2-(1,1-dimethylethyl)-6-[2-(2,3,6,7-tetrahydro-1,1,7,7-tetramethyl-1H,5H-benzo(ij)quinolizin-9-yl)ethenyl]-4H-pyran-4-ylidene]-propanedinitrile) in a small amount. When a process such as inkjet printing, roll coating, spin coating, is used to form a light emitting layer, polyphenylenevinylene (PPV)-based polymer or poly fluorene may be used for an organic luminescence layer.

On the organic luminescence layer, an electron transport layer is positioned. Such an electron transport layer requires a material which has a high efficiency for electrons injected from a cathode positioned thereon, and can efficiently transport the injected electrons. For this, a material having a high electron affinity, a high electron mobility, and a high electron stability is required. The examples of an electron transport material satisfying these conditions may include Al complex of 8-hydroxyquinoline; complex including $Alq_3$; organic radical compound; and hydroxyflavone-metal complex, but the present invention is not limited thereto.

On the electron transport layer, an electron injection layer is layered. The electron injection layer may be manufactured by using a metal complex compound (such as Balq, Alq3, Be(bq)2, Zn(BTZ)2, Zn(phq)2, PBD, spiro-PBD, TPBI, and Tf-6P) or a low molecular material including an aromatic compound having an imidazole ring or a boron compound. Herein, the electron injection layer may be formed in a thickness range of 100 Å to 300 Å.

On the electron injection layer, a cathode is positioned. Such a cathode performs a role of injecting electrons into the electron injection layer. As a material for the cathode, the same material as that used for an anode may be used. In order to achieve efficient electron injection, a metal having a low work function is more preferable. Especially, metals such as tin, magnesium, indium, calcium, sodium, lithium, aluminum, silver, or alloys thereof may be used. Further, a double-layered electrode (e.g., lithiumfluoride and aluminum, lithium oxide and aluminum, and strontium oxide and aluminum) with a thickness of 100 μm or less may be used.

The OLED according to the present invention may be manufactured in a front luminescent type, a rear luminescent type, or a both-side luminescent type according to its materials.

Meanwhile, the present invention provides a terminal which includes a display device and a control part for driving the display device, the display device including the above described organic electronic device. The terminal means a wired/wireless communication terminal which is currently used or will be used in the future. The above described terminal according to the present invention may be a mobile communication terminal such as a cellular phone, and may include all kinds of terminals such as a PDA, an electronic dictionary, a PMP, a remote control, a navigation unit, a game player, various kinds of TVs, and various kinds of computers.

Example

Hereinafter, the present invention will be described more specifically with reference to Preparation Examples and Experimental Examples. However, the following examples are only for illustrative purposes and are not intended to limit the scope of the invention.

Preparation Example

Hereinafter, Preparation Examples or Synthesis Examples of the compounds including a 5-membered heterocycle, represented by Formula 1, will be described. However, since there are many compounds including a 5-membered heterocycle, represented by Formula 1, one compound or two compounds from among the compounds will be exemplified. The person skilled in the art of the invention should realize that other compounds including a 5-membered heterocycle can be prepared through Preparation Examples as described below although they are not exemplified.

Synthesis Method

Hereinafter, Preparation Examples or Synthesis Examples of the compounds including a 5-membered heterocycle, represented by Formula 1, will be described. However, since there are many compounds including a 5-membered heterocycle, represented by Formula 1, one compound or two compounds from among the compounds will be exemplified. A person skilled in the art of the invention should realize that other compounds including a 5-membered heterocycle can be prepared through Preparation Examples as described below although they are not exemplified.

Synthesis Example 1

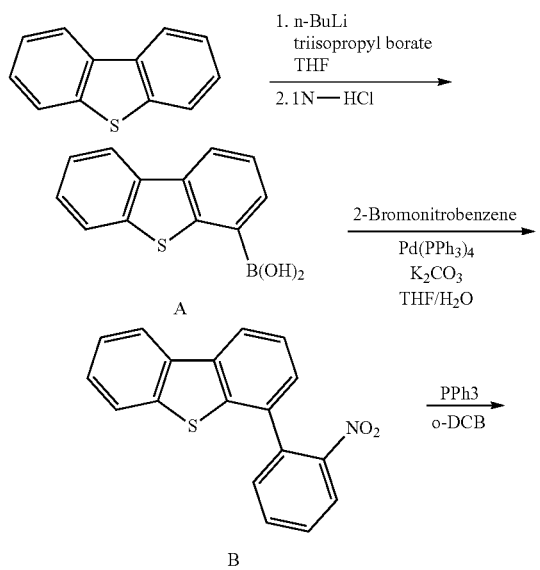

-continued

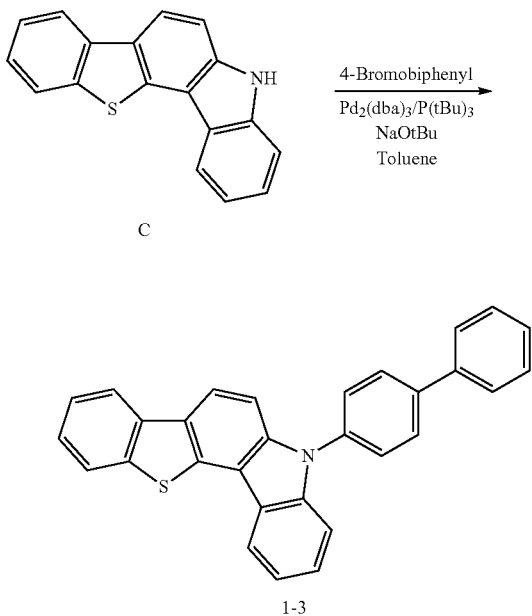

Synthesis Method of Intermediate A

Dibenzothiophene was dissolved in tetrahydrofuran, and the temperature of the reaction product was lowered to −78° C. n-BuLi (2.5 M in hexane) was slowly added thereto, and the mixture was stirred for 1 hour at 0° C. Then, the temperature of the product was lowered to −78° C., and a triisopropyl borate solution dissolved in tetrahydrofuran was dropped thereto, followed by stirring for 12 hours at room temperature. After the completion of the reaction, the resultant product was added with 1N-HCl aqueous solution, stirred for 30 minutes, and extracted with ether. From the extract, a small amount of water was removed by magnesium sulfate anhydrous, followed by vacuum-filtration. Then, the product obtained after concentration of an organic solvent was purified by column chromatography to give a required intermediate A (yield: 71%).

Synthesis Method of Intermediate B

The intermediate A obtained from the previous step, 2-bromonitrobenzene, Pd(PPh3)4, and potassium carbonate ($K_2CO_3$) were dissolved in tetrahydrofuran and a small amount of water, followed by reflux for 24 hours. After the completion of the reaction, the reaction product was cooled to room temperature, extracted with dichloromethane ($CH_2Cl_2$), and washed with water. From the extract, a small amount of water was removed by magnesium sulfate anhydrous, followed by vacuum-filtration. Then, the product obtained after concentration of an organic solvent was purified by column chromatography to give a required intermediate B (yield: 87%).

Synthesis Method of Intermediate C

The intermediate B obtained from the previous step, and triphenylphosphine were dissolved in o-DCB(o-dichlorobenzene), followed by reflux for 24 hours. After the completion of the reaction, vacuum distillation was carried out for removal of a solvent. Then, the concentrated product was purified by column chromatography to give a required intermediate C (yield: 61%).

Synthesis Method of Compound 1-3

The intermediate C obtained from the previous step, 4-bromobiphenyl, Pd2(dba)3, P(tBu)3, and NaOtBu were dissolved in a toluene solvent, followed by reflux for 6 hours at 110° C. After the completion of the reaction, the reaction product was subjected to vacuum filtration through celite and silica gel by using a hot toluene solvent. The temperature was cooled to room temperature, and the deposited product was recrystallized again by toluene and acetone so as to give a required compound 1-3 (yield: 70%).

2. Synthesis of Compounds 2-1 and 3-1 Represented by Formulas 9 and 10

Synthesis Example 2

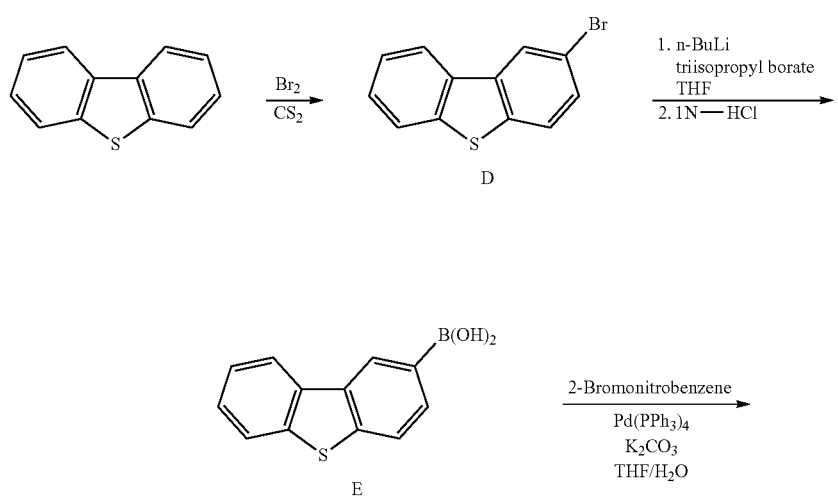

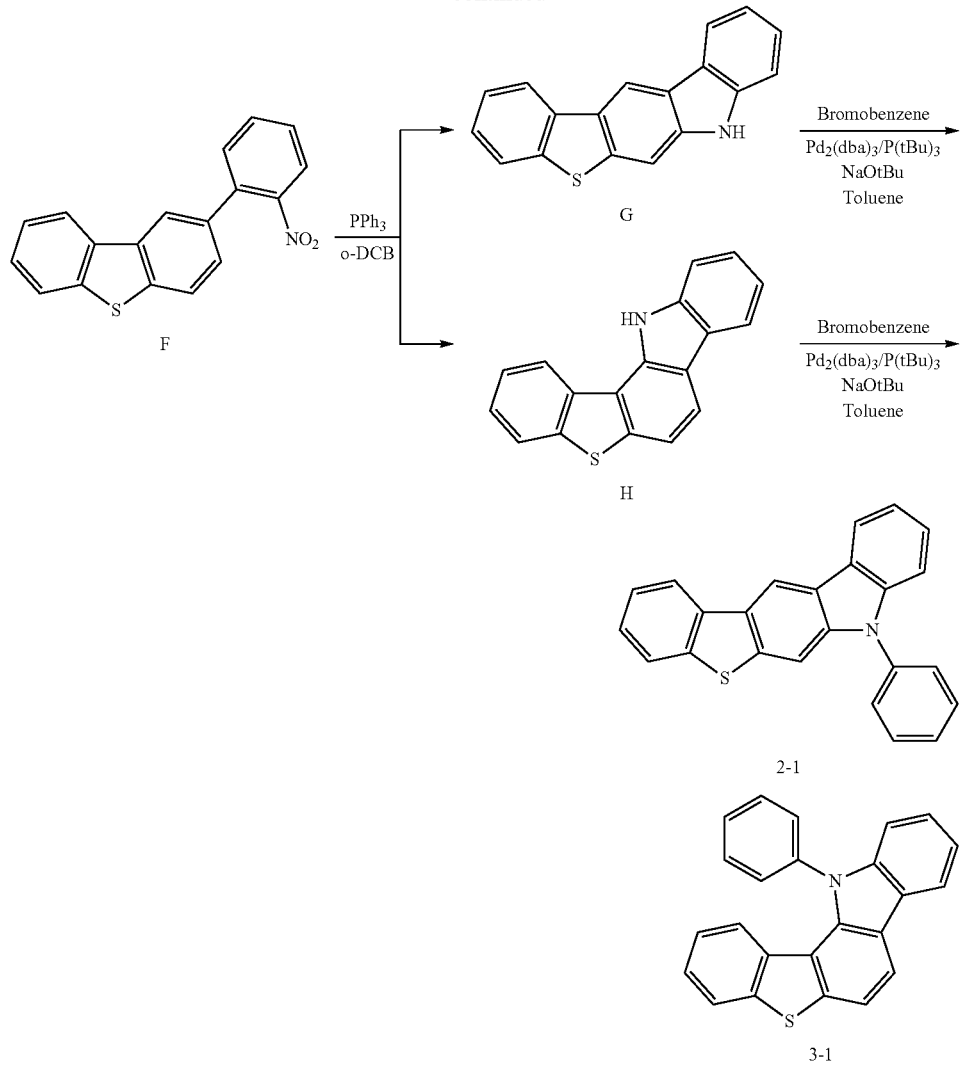

Synthesis Method of Intermediate D

Dibenzothiophene was dissolved in carbondisulfide (CS$_2$), and bromine was slowly dropped thereto. The resultant mixture was stirred at room temperature for 12 hours. After the completion of the reaction, the product produced by concentration of an organic solvent through a decompressor was recrystallized by an ethanol solvent so as to give a required intermediate D (yield: 86%).

Synthesis Method of Intermediate E

The intermediate D obtained from the previous step was dissolved in anhydrous tetrahydrofuran, and the temperature of the reaction product was lowered to −78° C. n-BuLi (2.5 M in hexane) was slowly dropped thereto, and the reaction temperature was stirred at 0° C. for 1 hour. Then, the temperature of the reaction product was lowered to −78° C., and a triisopropyl borate solution dissolved in tetrahydrofuran was dropped thereto, followed by stirring for 12 hours at room temperature. After the completion of the reaction, the resultant product was added with 1N-HCl aqueous solution, stirred for 30 minutes, and extracted with ether. From the extract, a small amount of water was removed by magnesium sulfate anhydrous, followed by vacuum-filtration. Then, the product obtained after concentration of an organic solvent was purified by column chromatography to give a required intermediate E (yield: 82%).

Synthesis Method of Intermediate F

The intermediate E obtained from the previous step, 2-bromonitrobenzene, Pd(PPh3)4, and potassium carbonate (K$_2$CO$_3$) were dissolved in tetrahydrofuran and a small amount of water, followed by reflux for 24 hours. After the completion of the reaction, the reaction product was cooled to room temperature, extracted with dichloromethane (CH$_2$Cl$_2$), and washed with water. From the extract, a small amount of water was removed by magnesium sulfate anhydrous, followed by vacuum-filtration. Then, the product obtained after concentration of an organic solvent was purified by column chromatography to give a required intermediate F (yield: 87%).

Synthesis Method of Intermediates G and H

The intermediate F obtained from the previous step, and triphenylphosphine were dissolved in o-DCB, followed by reflux for 24 hours. After the completion of the reaction, vacuum distillation was carried out for removal of a solvent. Then, the concentrated product was purified by column chromatography to give required intermediates G and H (yield: 61%, ratio of G to H=6:4).

Synthesis Method of Compound 2-1

The intermediate G obtained from the previous step, bromobenzene, Pd2(dba)3, P(tBu)3, and NaOtBu were dissolved in a toluene solvent, followed by reflux for 6 hours at 110° C. After the completion of the reaction, the reaction product was subjected to vacuum filtration through celite and silica gel by using a hot toluene solvent. The temperature was cooled to room temperature, and the deposited product was recrystallized again by toluene and acetone so as to give a required compound 2-1 (yield: 68%).

Synthesis Method of Compound 3-1

The intermediate H obtained from the previous step, bromobenzene, Pd2(dba)3, P(tBu)3, and NaOtBu were dissolved in a toluene solvent, followed by reflux for 6 hours at 110° C. After the completion of the reaction, the reaction product was subjected to vacuum filtration through celite and silica gel by using a hot toluene solvent. The temperature was cooled to room temperature, and the deposited product was recrystallized again by toluene and acetone so as to give a required compound 3-1 (yield: 62%).

3. Synthesis of Compounds 4-3 and 5-3 Represented by Formulas 11 and 12

Synthesis Example 3

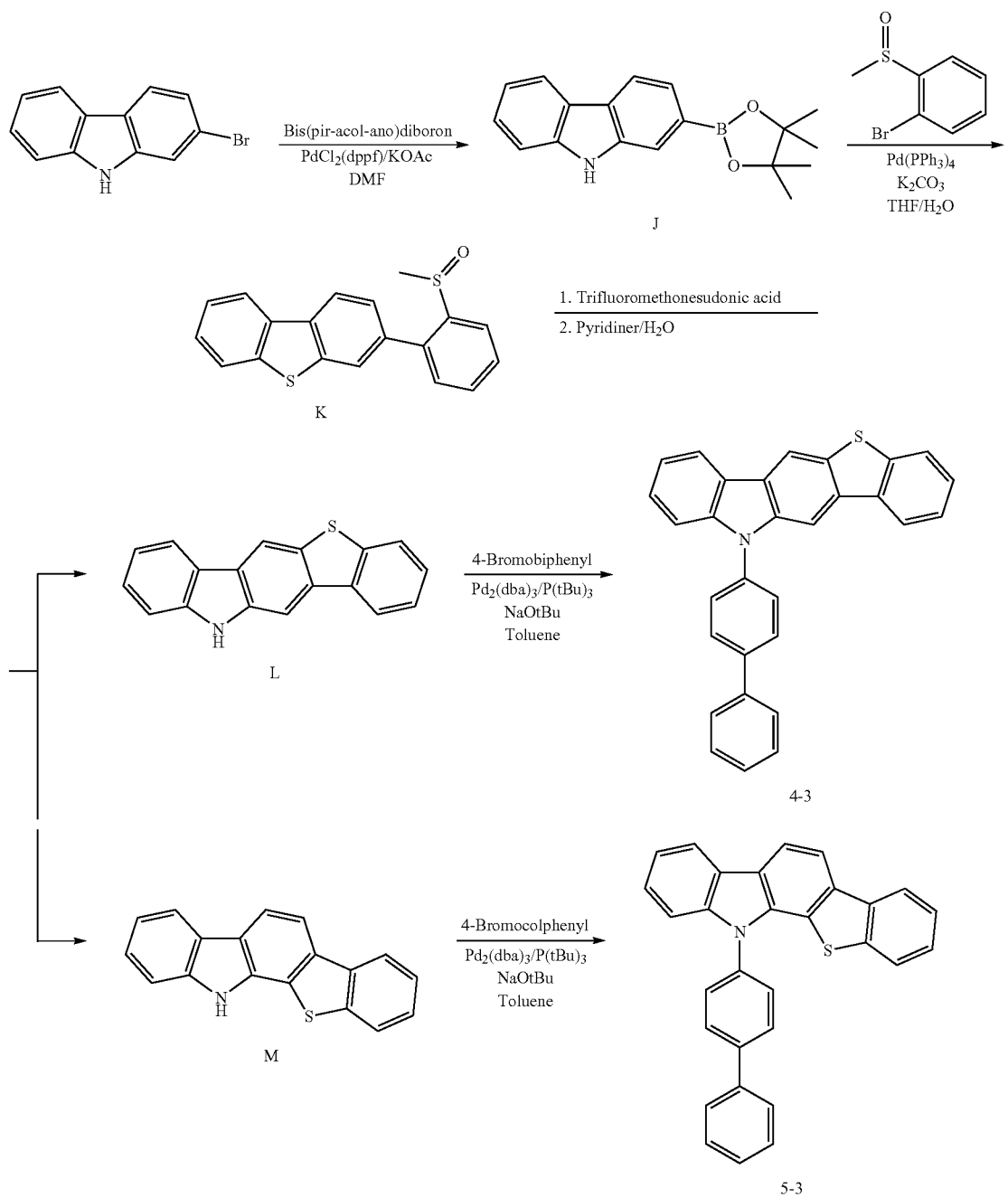

Synthesis Method of Intermediate J

2-Bromocarbazole, bis(pinacolato)diboron, palladium chloride (PdCl$_2$) (dppf), and KOAc were dissolved in dimethylformamide, followed by stirring at 130° C. for 3 hours. After the completion of the reaction, the reaction product was cooled to room temperature, and then added with ether and distilled water, followed by stirring at room temperature. An organic was separated from a water layer, and the separation was repeatedly carried out twice by the same method. The resultant product produced through the concentration of the organic layer was recrystallized by acetonitrile so as to give a required intermediate J (yield: 38%).

Synthesis Method of Intermediate K

The intermediate J obtained from the previous step, 1-bromo-2-(methylsulfinyl)benzene, Pd(PPh3)4, and potassium carbonate were dissolved in tetrahydrofuran and a small amount of water, followed by reflux for 24 hours. After the completion of the reaction, the reaction product was cooled to room temperature, extracted with dichloromethane (CH$_2$Cl$_2$), and washed with water. From the extract, a small amount of water was removed by magnesium sulfate anhydrous, followed by vacuum-filtration. Then, the product obtained after concentration of an organic solvent was purified by column chromatography to give a required intermediate K (yield: 51%).

Synthesis Method of Intermediates L and M

The intermediate K obtained from the previous step was dissolved in trifluoromethanesulfonic acid solvent, followed by stirring at room temperature for 48 hours. After the completion of the reaction, the reaction product was added with a mixed solvent of water and pyridine, followed by reflux for 20 minutes. The reaction product was cooled to room temperature, extracted with dichloromethane (CH$_2$Cl$_2$), and washed with water. From the extract, a small amount of water was removed by magnesium sulfate anhydrous, followed by vacuum-filtration. Then, the product obtained after concentration of an organic solvent was purified by column chromatography to give required intermediates L and M (yield: 38%, ratio of L to M=8:2).

Synthesis Method of Compound 4-3

The intermediate L obtained from the previous step, 4-bromobiphenyl, Pd2(dba)3, P(tBu)3, and NaOtBu were dissolved in a toluene solvent, followed by reflux for 6 hours at 110° C. After, the completion of the reaction, the reaction product was subjected to vacuum filtration through celite and silica gel by using a hot toluene solvent. The temperature was cooled to room temperature, and the deposited product was recrystallized again by toluene and acetone so as to give a required compound 4-3 (yield: 77%).

Synthesis Method of Compound 5-3

The intermediate M obtained from the previous step, 4-bromobiphenyl, Pd2(dba)3, P(tBu)3, and NaOtBu were dissolved in a toluene solvent, followed by reflux for 6 hours at 110° C. After, the completion of the reaction, the reaction product was subjected to vacuum filtration through celite and silica gel by using a hot toluene solvent. The temperature was cooled to room temperature, and the deposited product was recrystallized again by toluene and acetone so as to give a required compound 5-3 (yield: 63%).

4. Synthesis of Compound 6-1 Represented by Formula 13

Synthesis Example 4

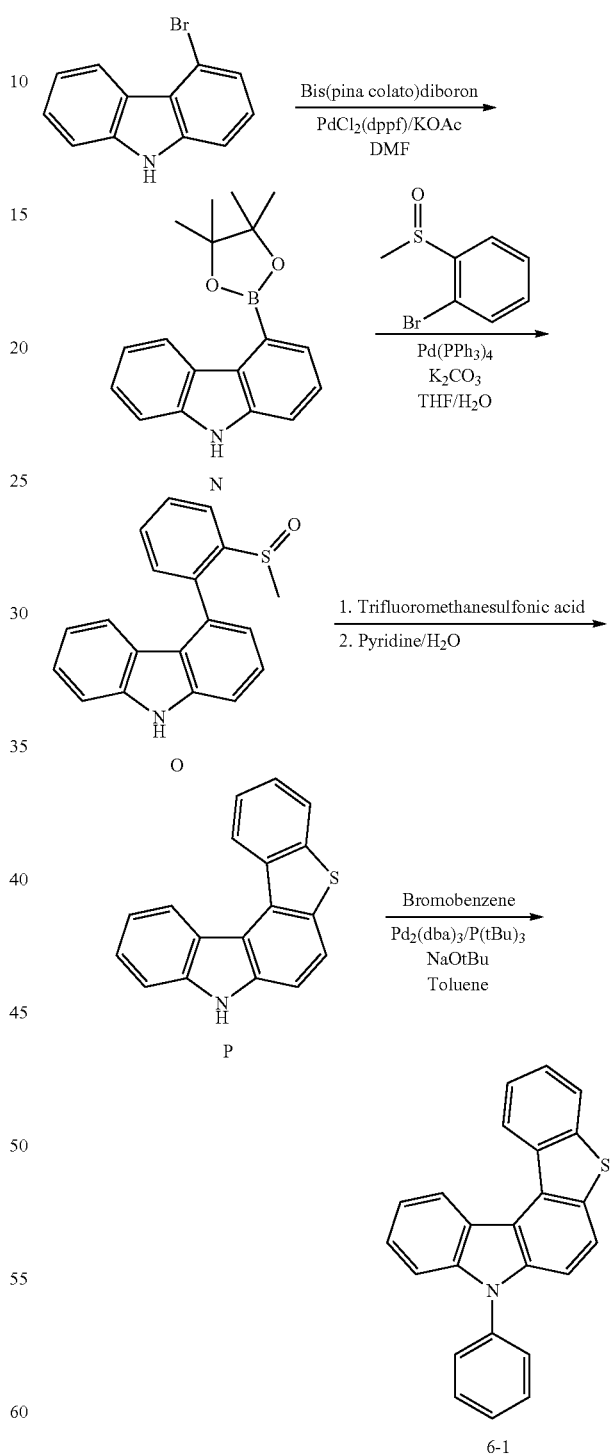

Synthesis Method of Intermediate N

1-Bromocarbazole, bis(pinacolato)diboron, palladium chloride (PdCl$_2$)(dppf), and KOAc were dissolved in dimethylformamide, followed by stirring at 130° C. for 3 hours.

After the completion of the reaction, the reaction product was cooled to room temperature, and then added with ether and distilled water, followed by stirring at room temperature. An organic was separated from a water layer, and the separation was repeatedly carried out twice by the same method. The resultant product produced through the concentration of the organic layer was recrystallized by acetonitrile so as to give a required intermediate N (yield: 35%).

Synthesis Method of Intermediate O

The intermediate N obtained from the previous step, 1-bromo-2-(methylsulfinyl)benzene, Pd(PPh3)4, and potassium carbonate were dissolved in tetrahydrofuran and a small amount of water, followed by reflux for 24 hours. After the completion of the reaction, the reaction product was cooled to room temperature, extracted with dichloromethane (CH$_2$Cl$_2$), and washed with water. From the extract, a small amount of water was removed by magnesium sulfate anhydrous, followed by vacuum-filtration. Then, the product obtained after concentration of an organic solvent was purified by column chromatography to give a required intermediate O (yield: 62%).

Synthesis Method of Intermediate P

The intermediate O obtained from the previous step was dissolved in trifluoromethanesulfonic acid solvent, followed by stirring at room temperature for 48 hours. After the completion of the reaction, the reaction product was added with a mixed solvent of water and pyridine, followed by reflux for 20 minutes. The reaction product was cooled to room temperature, extracted with dichloromethane (CH$_2$Cl$_2$), and washed with water. From the extract, a small amount of water was removed by magnesium sulfate anhydrous, followed by vacuum-filtration. Then, the product obtained after concentration of an organic solvent was purified by column chromatography to give a required intermediates P (yield: 42%).

Synthesis Method of Compound 6-1

The intermediate P obtained from the previous step, bromobenzene, Pd2(dba)3, P(tBu)3, and NaOtBu were dissolved in a toluene solvent, followed by reflux for 6 hours at 110° C. After, the completion of the reaction, the reaction product was subjected to vacuum filtration through celite and silica gel by using a hot toluene solvent. The temperature was cooled to room temperature, and the deposited product was recrystallized again by toluene and acetone so as to give a required compound 6-1 (yield: 75%).

Fabrication Test of Organic EL Device

An OLED was manufactured according to a conventional method by using each of compounds 1-3, 2-1, 3-1, 4-3, 5-3, and 6-1 obtained by synthesis as a light emitting host material for a light emitting layer. First, on a glass substrate, an ITO layer (anode) was formed with a thickness of 10 nm. On the ITO layer (anode), a copper phthalocyanine (hereinafter, referred to as CuPc) film as a hole injection layer was vacuum-deposited. Then, on this film, 4,4-bis[N-(1-naphthyl)-N-phenylamino]biphenyl (hereinafter, referred to as a-NPD) as a hole transport compound was vacuum-deposited with a thickness of 30 nm so as to form a hole transport layer. After the hole transport layer was formed, each of the compounds 1-3, 2-1, 3-1, 4-3, 5-3, and 6-1 as a phosphorescence host material was deposited on the hole transport layer so as to form a light emitting layer. At the same time, as a phosphorescent Ir metal complex dopant, tris(2-phenylpyridine)iridium (hereinafter, referred to as Ir(ppy)$_3$) was added. Herein, in the light emitting layer, the concentration of Ir(ppy)$_3$ was 5 wt %. As a hole blocking layer, (1,1-bisphenyl)-4-olato)bis(2-methyl-8-quinolinolato)aluminum (hereinafter, referred to as BAlq) was vacuum-deposited with a thickness of 10 nm, and then as an electron injection layer, tris(8-quinolinol)aluminum (hereinafter, referred to as Alq$_3$) was film-formed with a thickness of 40 nm. Then, LiF (alkali-metal halide) was deposited with a thickness of 0.2 nm, and Al was deposited with a thickness of 150 nm. The Al/LiF was used as a cathode while the OLED was fabricated.

[Formula 14]

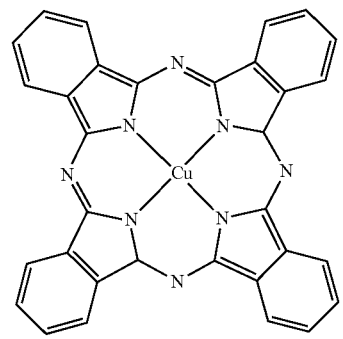

CuPc

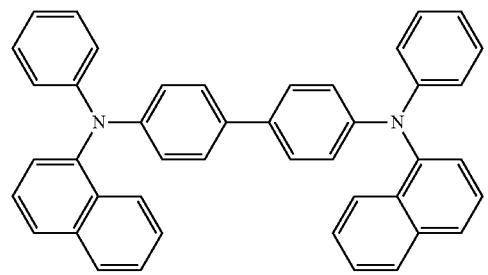

a-NPD

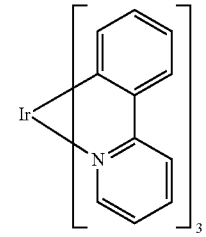

Ir(ppy)$_3$

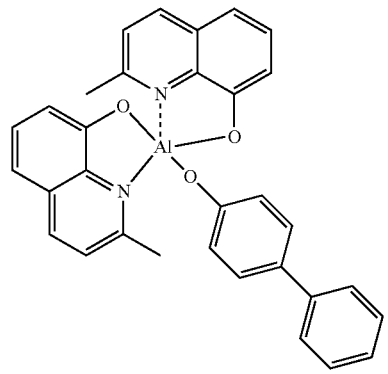

BAlq

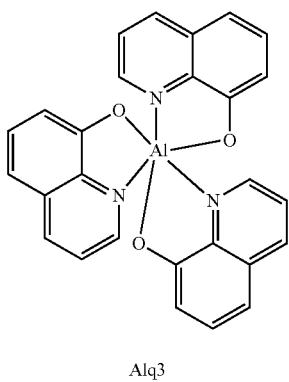

Alq3

Comparison Example

For comparison, instead of the inventive compound, a compound (hereinafter, referred to as CBP) represented by Formula below was used as a light emitting host material so as to fabricate an OLED with the same structure as that of Test Example.

[Formula 15]

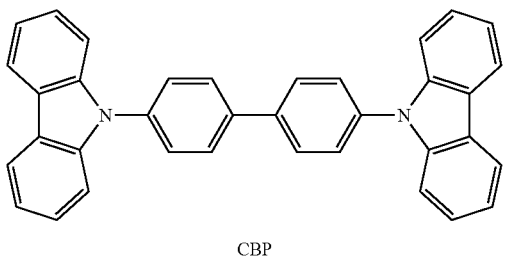

CBP

From the results noted in Table 1, it can be seen that in an OLED using the inventive material for the OLED, it is possible to obtain long-life green light with a high efficiency, and an improved color purity. Thus, the inventive material as a green phosphorescence host material for an OLED can significantly improve the luminous efficiency and lifetime.

It is natural that even though the inventive compounds are applied to other organic material layers of an OLED, e.g., a light emitting layer, an auxiliary light emitting layer, an electron injection layer, an electron transport layer, and a hole injection layer as well as a hole transport layer, it is possible to achieve the same effects.

Although a preferred embodiment of the present invention has been described for illustrative purposes, those skilled in the art will appreciate that various modifications, additions and substitutions are possible, without departing from the scope and spirit of the invention as disclosed in the accompanying claims. Therefore, the embodiments disclosed in the present invention are intended to illustrate the scope of the technical idea of the present invention, and the scope of the present invention is not limited by the embodiment.

The scope of the present invention shall be construed on the basis of the accompanying claims in such a manner that all of the technical ideas included within the scope equivalent to the claims belong to the present invention.

What is claimed is:

1. A compound represented by Formula below, or a derivative compound thereof:

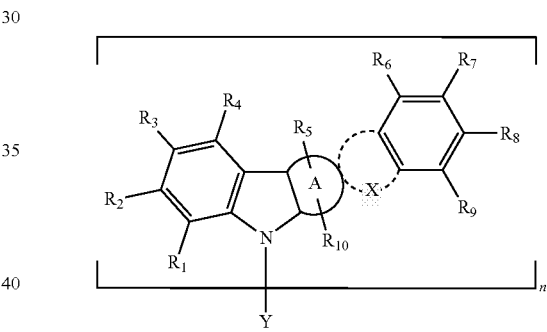

wherein each of $R_1$ through $R_{10}$ is a hydrogen atom;
A is an aryl having 6 carbon atoms;
a ring comprising X is thiophene;
Y is a substituted or unsubstituted $C_5$-$C_{60}$ heteroaryl group having nitrogen; and
n is 1.

TABLE 1

| | Host material of light emitting layer | Voltage (V) | current density (mA/cm²) | luminance (cd/m²) | luminous efficiency (cd/A) | chromaticity coordinates (x, y) |
|---|---|---|---|---|---|---|
| Example 1 | compound 1-3 | 5.5 | 0.35 | 106 | 51.3 | (0.30, 0.60) |
| Example 2 | compound 2-1 | 5.8 | 0.33 | 107 | 47.3 | (0.30, 0.60) |
| Example 3 | compound 3-1 | 5.9 | 0.31 | 105 | 45.2 | (0.32, 0.61) |
| Example 4 | compound 4-3 | 5.9 | 0.31 | 105 | 44.2 | (0.30, 0.60) |
| Example 5 | compound 5-3 | 5.6 | 0.32 | 107 | 48.3 | (0.31, 0.61) |
| Example 6 | compound 6-1 | 6.1 | 0.31 | 103 | 43.9 | (0.30, 0.60) |
| Comparative Example 1 | CBP | 6.1 | 0.31 | 101 | 32.6 | (0.33, 0.61) |

2. The compound as claimed in claim 1, wherein the compound is any one of compounds below:
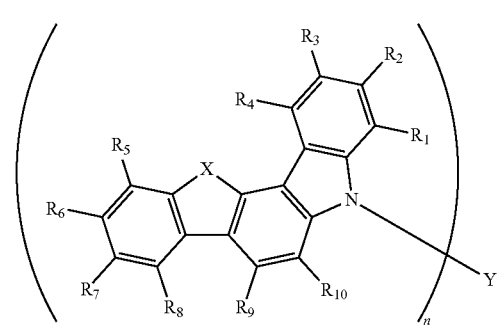
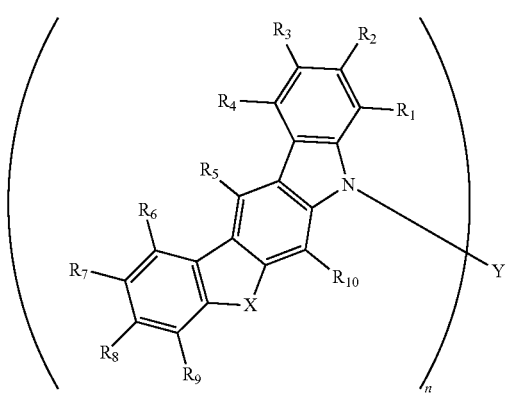
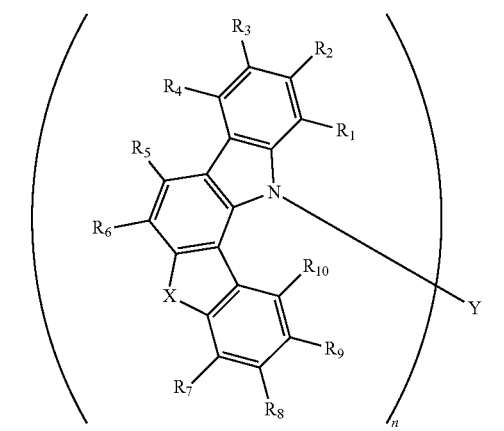
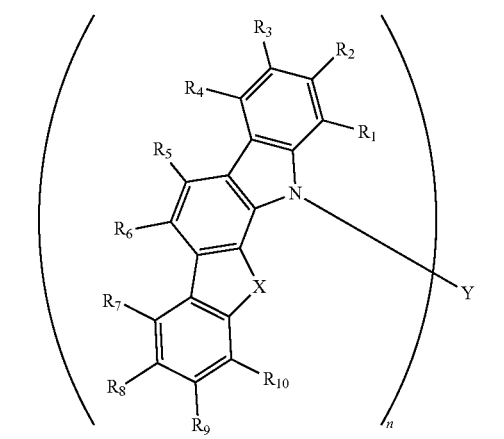
-continued
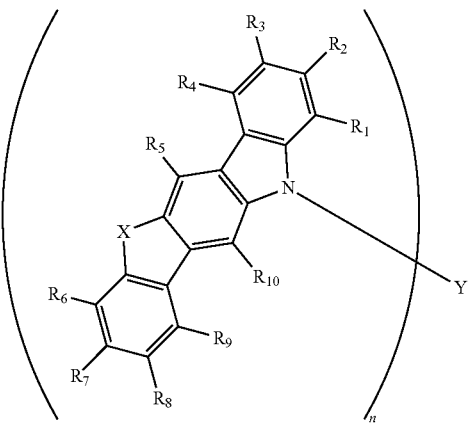
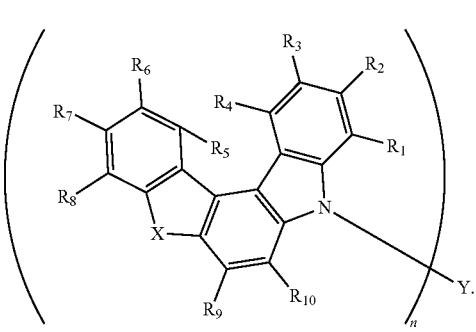
3. The compound as claimed in claim 2, wherein the compound is any one of compounds below:
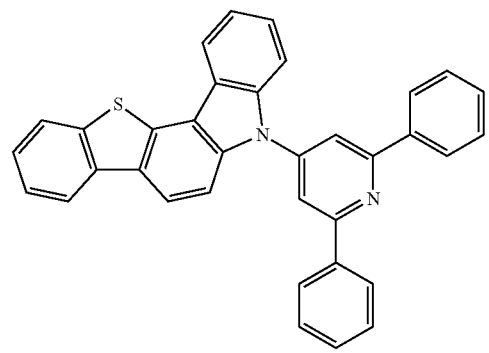
1-6
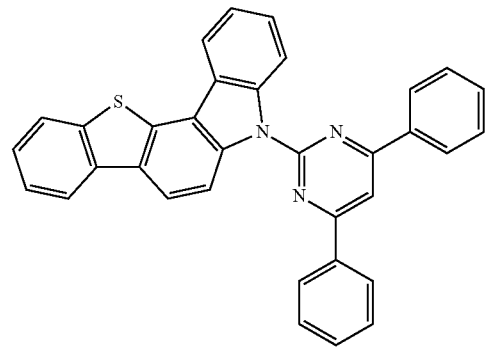
1-7

1-8
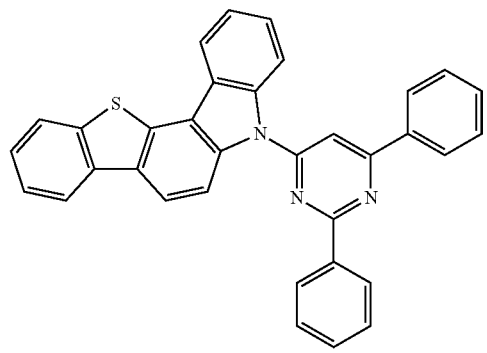
1-9
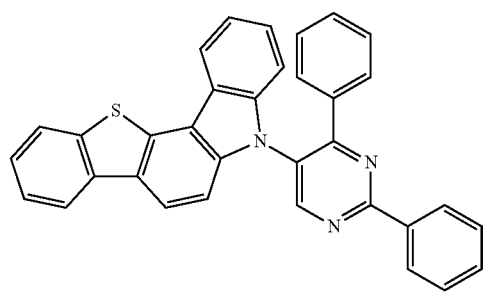
1-10
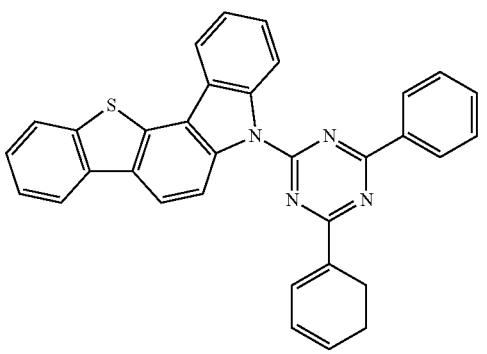
2-6
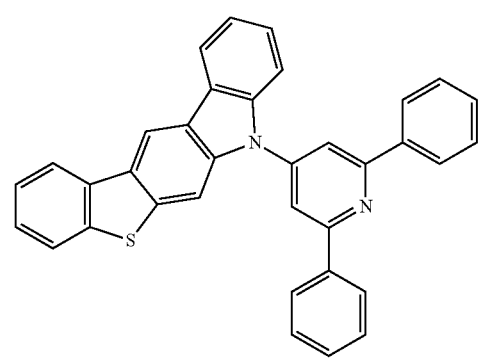
2-7
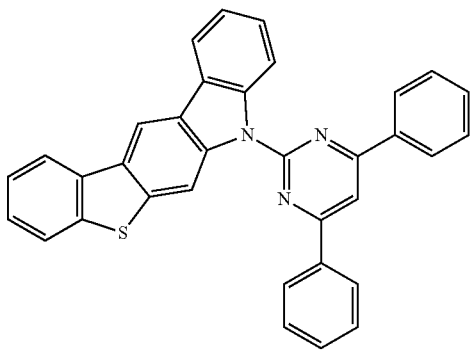
2-8
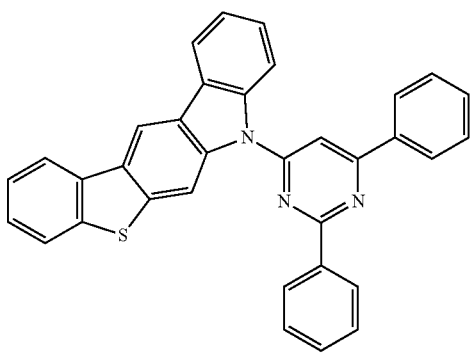
2-9
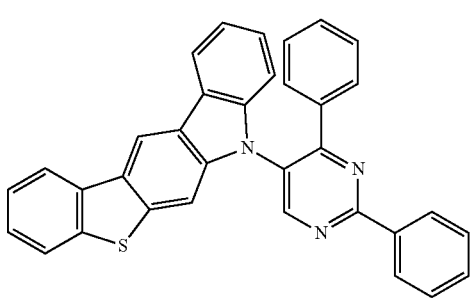
2-10
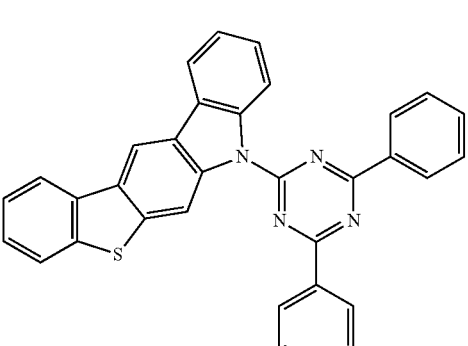

3-6
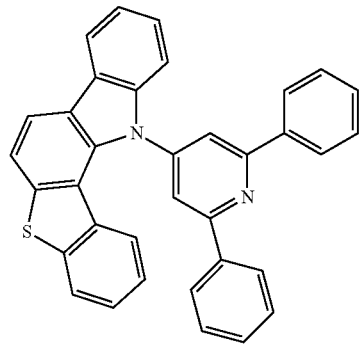
3-7
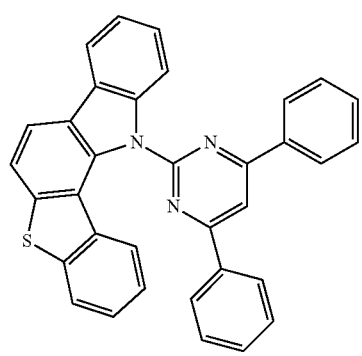
3-8
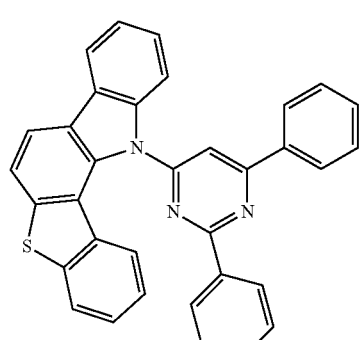
3-9
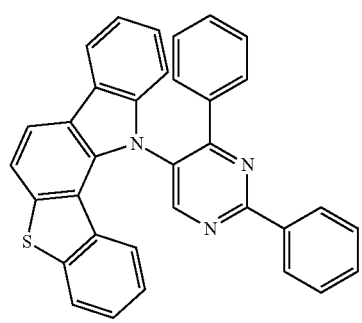
3-10
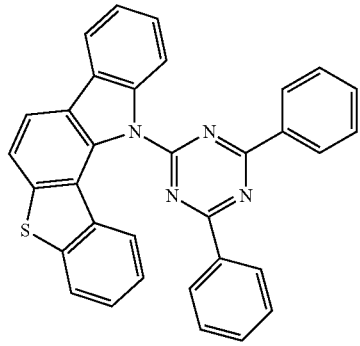
4-6
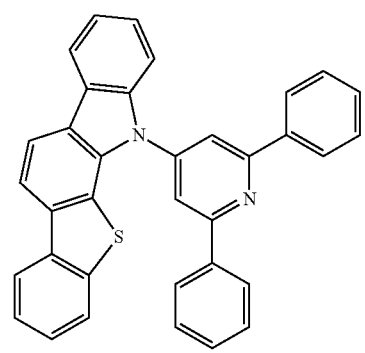
4-7
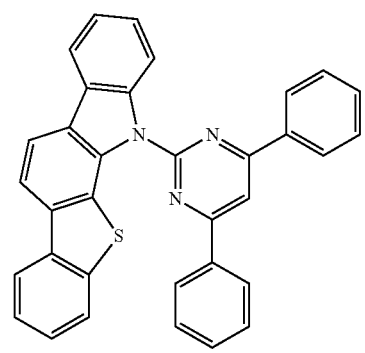
4-8
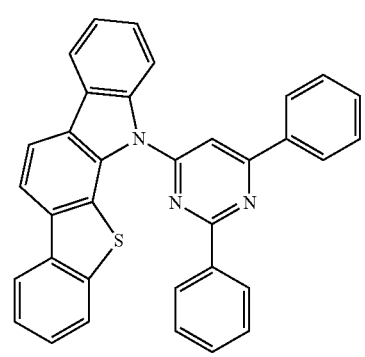

4-9
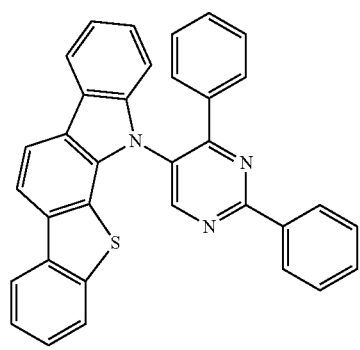
4-10
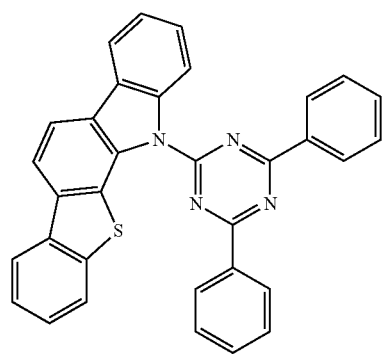
5-6
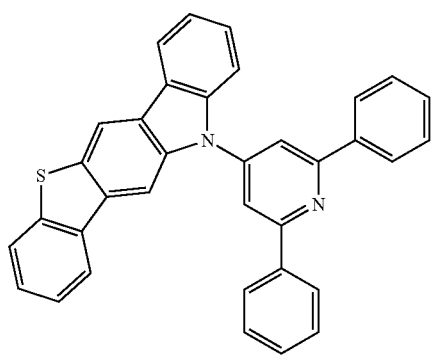
5-7
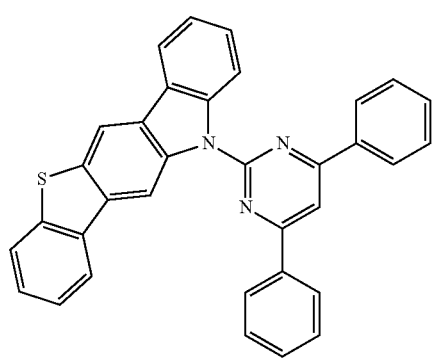
5-8
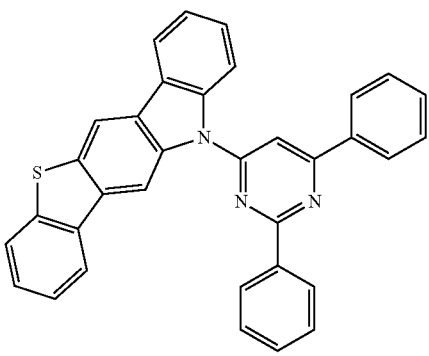
5-9
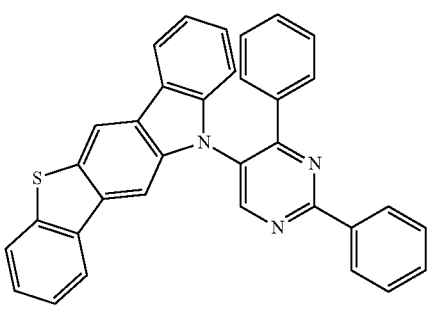
5-10
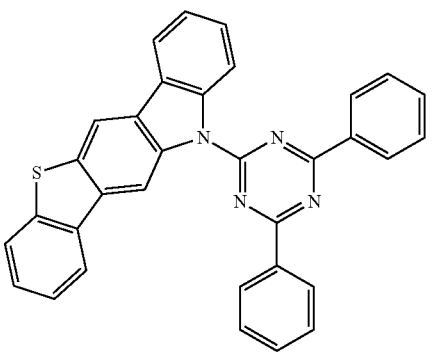
6-6
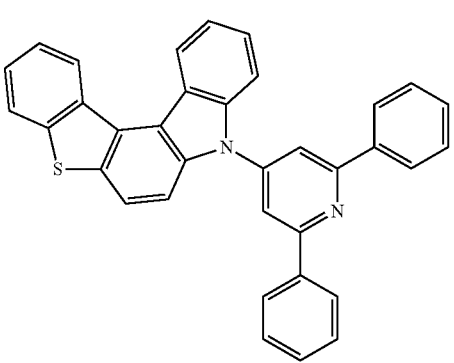

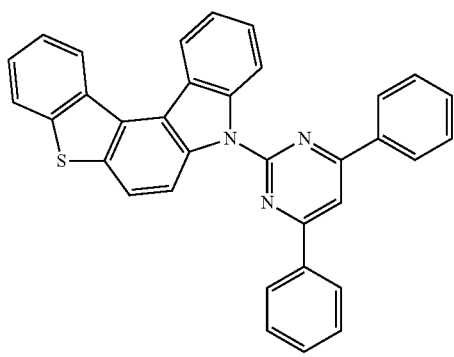

6-7

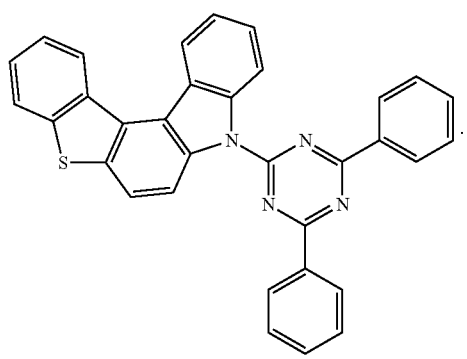

6-10

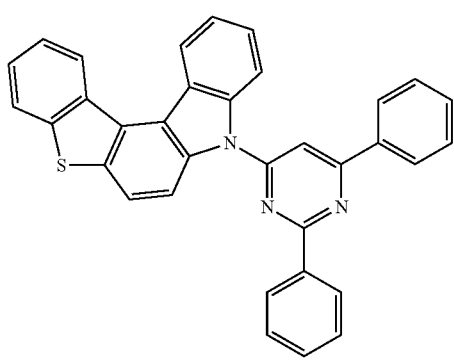

6-8

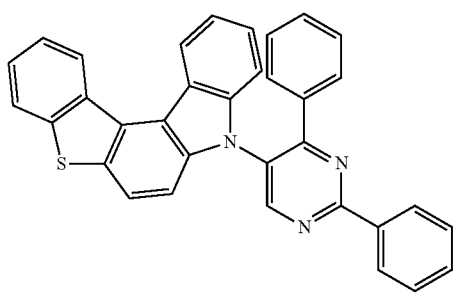

6-9

4. An organic electronic device comprising one or more organic material layers comprising the compound as claimed in claim 1.

5. The organic electronic device as claimed in claim 4, wherein the organic material layers are formed by a soluble process of the compound.

6. The organic electronic device as claimed in claim 4, wherein the organic electronic device is an organic light emitting diode in which a first electrode, said one or more organic material layers, and a second electrode are sequentially layered.

7. The organic electronic device as claimed in claim 6, wherein the organic material layers comprise any one of a hole injection layer, a hole transport layer, a light emitting layer, an electron transport layer, and an electron injection layer.

8. The organic electronic device as claimed in claim 6, wherein the one or more organic material layers comprise a light emitting layer, and in the light emitting layer, the compound is used as a host or dopant material.

9. A terminal comprising a display device and a control part for driving the display device, the display device comprising the organic electronic device as claimed in claim 6.

10. The terminal as claimed in claim 9, wherein the organic electronic device is any one of an organic light emitting diode (OLED), an organic solar cell, an organic photo conductor (OPC) drum, and an organic transistor (organic TFT).

* * * * *